(12) United States Patent
Insana et al.

(10) Patent No.: US 10,327,740 B2
(45) Date of Patent: Jun. 25, 2019

(54) RETRIEVING HIGH SPATIAL FREQUENCY INFORMATION IN SONOGRAPHY

(71) Applicant: The Board of Trustees of the University of Illinois, Urbana, IL (US)

(72) Inventors: Michael F. Insana, Urbana, IL (US); Sara Bahramianparchekoohi, Urbana, IL (US)

(73) Assignee: Board of Trustees of the University of Illinois, Urbana, IL (US)

(*) Notice: Subject to any disclaimer, the term of this patent is extended or adjusted under 35 U.S.C. 154(b) by 885 days.

(21) Appl. No.: 14/938,616

(22) Filed: Nov. 11, 2015

(65) Prior Publication Data

US 2016/0128671 A1    May 12, 2016

Related U.S. Application Data

(60) Provisional application No. 62/078,180, filed on Nov. 11, 2014.

(51) Int. Cl.
*A63F 9/24* (2006.01)
*A61B 8/08* (2006.01)
(Continued)

(52) U.S. Cl.
CPC .......... *A61B 8/5207* (2013.01); *A61B 8/5246* (2013.01); *A61B 8/5269* (2013.01);
(Continued)

(58) Field of Classification Search
CPC .... A61B 8/5246; A61B 8/5207; A61B 8/5238
See application file for complete search history.

(56) References Cited

U.S. PATENT DOCUMENTS 5,586,160 A    12/1996   Mascio
5,841,889 A *  11/1998   Seyed-Bolorforosh ......................
                                                        G01S 7/52046
                                                            382/128
(Continued)

OTHER PUBLICATIONS

Anderson, Martin E. et al., "The Detection of Breast Microcalcifications with Medical Ultrasound," The Journal of the Acoustical Society of America 101 (1), pp. 29-39 (Jan. 1997).
(Continued)

*Primary Examiner* — Steve Rowland
(74) *Attorney, Agent, or Firm* — Lowenstein Sandler LLP

(57) ABSTRACT

An imaging system includes a display device and a transducer to transmit acoustic pulses modulated with a carrier frequency and to collect at least a portion of a high-frequency backscatter signal comprising radio frequency (RF) data. A processing device is operatively coupled to the transducer probe and to the display device, and to: calculate a summation of a square of a real part and a square of an imaginary part of the backscatter signal, to generate an envelope signal including a mode-specific image suitable for display on the display device; calculate a difference of the square of the real part and the square of the imaginary part of the backscatter signal, to generate a complement signal; demodulate the complement signal to generate a low-frequency complement image suitable for display; and display the complement image on the display device to improve diagnostic imaging.

17 Claims, 18 Drawing Sheets

(51) Int. Cl.
　　　A61B 8/14　　　(2006.01)
　　　A61B 8/00　　　(2006.01)
(52) U.S. Cl.
　　　CPC ............... *A61B 8/085* (2013.01); *A61B 8/14* (2013.01); *A61B 8/463* (2013.01)

(56) References Cited

U.S. PATENT DOCUMENTS

| | | | | |
|---|---|---|---|---|
| 6,628,844 | B1* | 9/2003 | Benitz | G01S 13/9011 382/276 |
| 2003/0071750 | A1* | 4/2003 | Benitz | G01S 13/9011 342/25 R |
| 2013/0258805 | A1* | 10/2013 | Hansen | A61B 8/14 367/8 |
| 2015/0293222 | A1* | 10/2015 | Huang | G01S 15/8977 367/7 |

OTHER PUBLICATIONS

Haka, Abigail S. et al., "Identifying Microcalcifications in Benign and Malignant Breast Lesions by Probing Differences in their Chemical Composition using Raman Spectroscopy," Cancer Research 62, pp. 5375-5380 (Sep. 15, 2002).

Machado, Priscilla, "New Image Processing Technique for Evaluating Breast Microcalcifications," American Institute of Ultrasound in Medicine 31, pp. 885-893 (2012).

Kerlikowske, Karla, et al., "Effect of Age, Breast Density, and Family History on the Sensitivity of First Screening Mammography," JAMA 276, No. 1, pp. 33-38 (Jul. 3, 1996).

Nguyen, Nghia Q. et al., "Objective Assessment of Sonographic Quality I: Task Information," IEEE Transactions on Medical Imaging, vol. 32, No. 4, pp. 683-690 (Apr. 2013).

Nguyen, Nghia Q. et al., "Objective Assessment of Sonographic: Quality II Acquisition Information Spectrum," IEEE Transactions on Medical Imaging, vol. 32, No. 4, pp. 691-698 (Apr. 2013).

Bahramian, Sara, et al. "Analyzing the Performance of Ultrasonic B-Mode Imaging for Breast Lesion Diagnosis," SPIE Medical Imaging, pp. 90332A-1-90332A-11 (Mar. 19, 2014).

Bahramian, Sara, et al. "Retrieving High Spatial Frequency Information in Sonography for Improved Microcalcification Detection," SPIE Medical Imaging, pp. 90370W-1-90370W-10 (Mar. 11, 2014).

Abby, Craig K., "Observer Efficiency in Discrmination Tasks Simulating Malignant and Benign Breast Lesions Imaged with Ultrasound," IEEE Transactions on Medical Imaging, vol. 25, No. 2, pp. 198- 209 (Feb. 2006).

Jensen, Jorgen A., "User's Guide for the Field II Program," Technical University of Denmark, pp. 1-67 (May 21, 2014).

Sickles, Edward A., "Mammographic Detectability of Breast Microcalcifications," American Journal of Roentgenology 139, No. 5, pp. 913-918 (Nov. 1982).

Yeh, Eren, et al. "Prospective Comparison of Mammography, Sonography, and MRI in Patients Undergoing Neoadjuvant Chemotherapy for Palpable Breast Cancer," American Journal of Roentgenology 184, pp. 868-877 (2005.

Medical Ultrasound, Wikipedia, the free encyclopedia, download available via web page at http://en.wikipedia.org/wiki/medical_ultrasound, accessed on Oct. 16, 2015.

Freudenrich, Craig, "How Ultrasound Works," accessed at http://science.howstuffworks.com/ultrasound2.htm/ on Oct. 16, 2015.

* cited by examiner axial spatial frequency (mm$^{-1}$)

lateral spatial frequency (mm$^{-1}$)

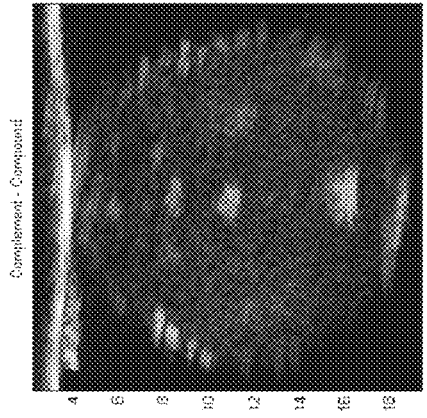
*FIG. 13C*
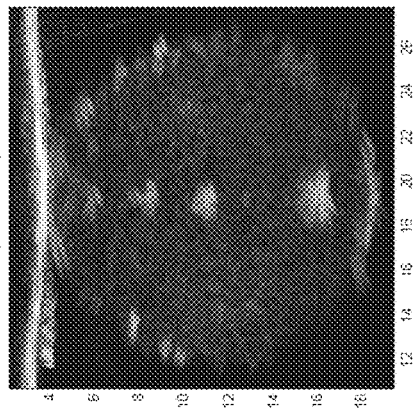
*FIG. 14C*
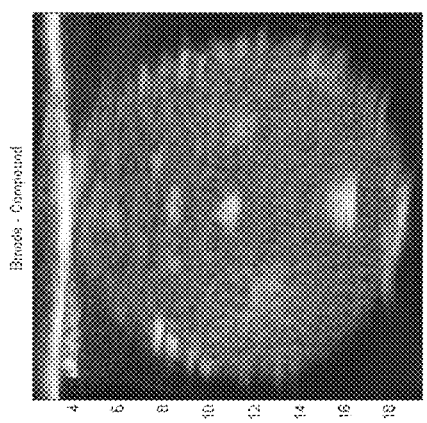
*FIG. 13B*
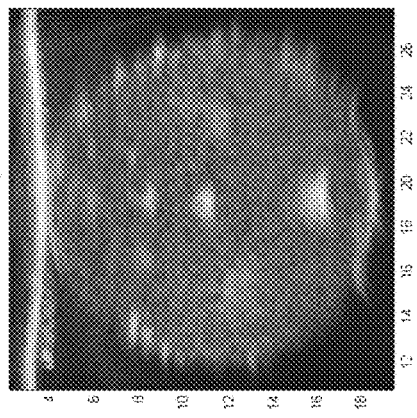
*FIG. 14B*
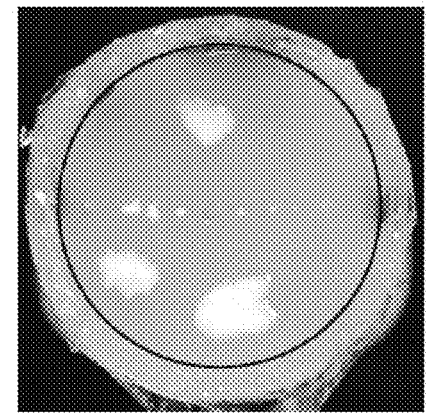
*FIG. 13A*
*FIG. 14A*

RETRIEVING HIGH SPATIAL FREQUENCY INFORMATION IN SONOGRAPHY

REFERENCE TO EARLIER FILED APPLICATION

This application claims the benefit under 35 U.S.C. § 119(e) of U.S. Provisional Patent Application No. 62/078,180, filed Nov. 11, 2014, which is incorporated herein, in its entirety, by this reference.

TECHNICAL FIELD

The present disclosure relates to sonography such as ultrasounds and corresponding imaging devices and modalities.

BACKGROUND

Breast microcalcifications are small (micrometer) calcium deposits that form in breast lesions. Size, number and arrangement of these deposits include important information about the malignancy and benignity of the breast lesions, making it critical to detect them in breast scans. Currently, mammography is the gold standard for detecting microcalcifications. However, in certain cases such as dense breast tissues, mammograms are ineffective and are often complemented by other modalities such as ultrasound. Ultrasound brightness (B)-scans illustrate microcalcification clusters as bright, high-contrast spots with the resolution limited by the size of speckle cells. Thus, distinguishing these reflections from speckle noise using ultrasound B-scans is also challenging.

To understand the reason for the poor performance of ultrasound in detecting microcalcifications, the inventors have previously studied the ability of the ultrasound B-mode processing in transferring diagnosis information from the patient to the B-mode image for a binary discrimination task. Information at each stage of the imaging process is defined based on an information theoretic measure, e.g., Kullback-Leibler divergence that is calculated as a distance between image data statistics under both hypotheses. Through this analysis, the inventors identified a spectrum that describes the ability of an imaging system to transfer information from an object to radio frequency (RF) data of a backscatter signal and also to the brightness (B)-mode (or other mode) image, at each spatial frequency.

Comparing the originally captured information in the RF data with the information available in the B-mode image revealed that the B-mode processing can eliminate as much as 50% of the information that can contribute to the diagnosis. These studies show that for small-area tasks such as microcalcification detection, the loss of information in the B-mode image is increased. This makes detection of microcalcifications in B-mode images quite challenging, even for a trained doctor.

BRIEF DESCRIPTION OF THE DRAWINGS

A more particular description of the disclosure briefly described above will be rendered by reference to the appended drawings. Understanding that these drawings only provide information concerning typical embodiments and are not therefore to be considered limiting of its scope, the disclosure will be described and explained with additional specificity and detail through the use of the accompanying drawings.

FIGS. 9A, 9B and 9C are images of a non-prewhitened feedback signal for the phantom breast lesion of FIG. 9, respectively: (A) complement; (B) B-mode; and (C) a combination of complement and B-mode.

FIGS. 9D, 9E and 9F are images of a prewhitened feedback signal for the phantom breast lesion of FIG. 9, respectively: (D) complement; (E) B-mode; and (F) a combination of complement and B-mode.

FIGS. 13A, 13B and 13C are images of the feedback signal of FIGS. 11A, 11B and 11C, but using angular compounding with five angular frames, to generate, respectively: (A) phantom lesion; (B) B-mode compound; and (C) complement compound.

FIGS. 14A, 14B and 14C are images of the feedback signal of FIGS. 11A, 11B and 11C, but using angular compounding with 13 angular frames, to generate, respectively: (A) phantom lesion; (B) B-mode compound; and (C) complement compound.

DETAILED DESCRIPTION

Figure 1:
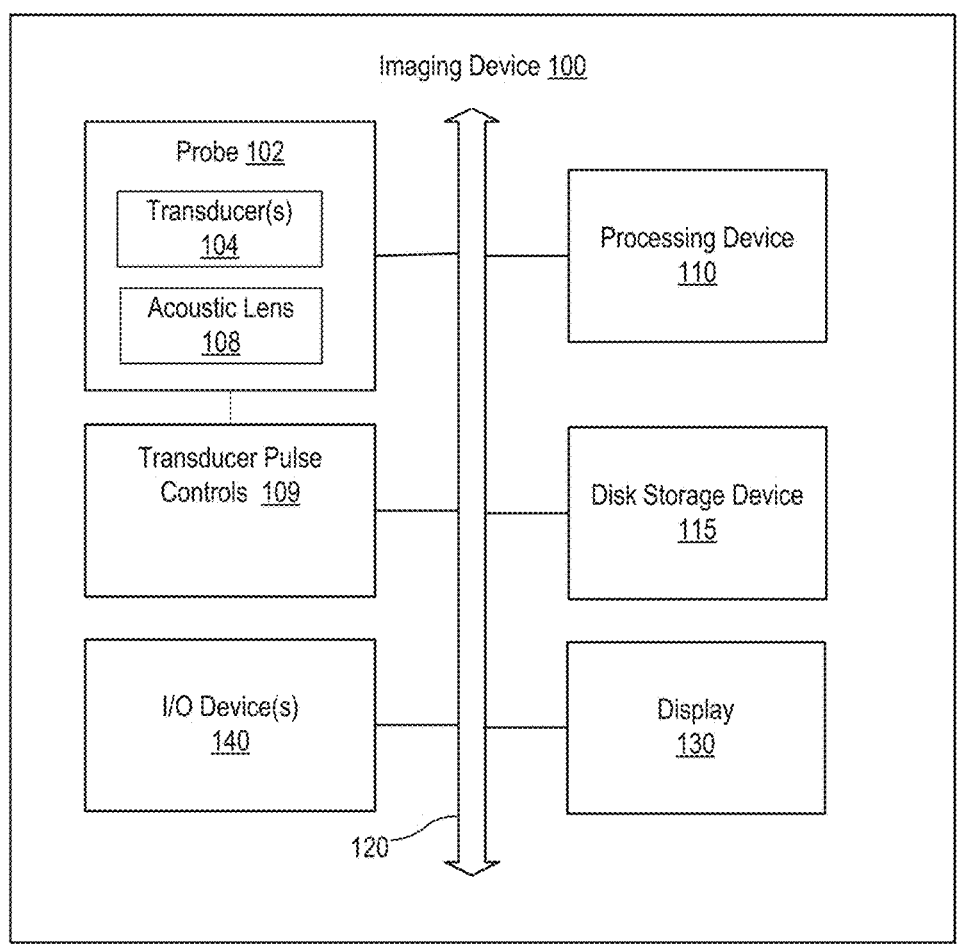
FIG. 1 is a diagram of an imagining device according to one embodiment of the present disclosure.

By way of introduction, the present disclosure relates to sonography such as ultrasounds and corresponding imaging devices and modalities. Ultrasound images are formed through a multi-stage process. In a first stage, acoustic pulses modulated with a carrier frequency are sonified at the region of interest in the body. Acoustic impedance gradients, as well as sub-resolution scattering agents in the tissue, create a backscatter signal that is at least partially collected by a transducer. This high-frequency signal is denoted as radio-frequency (RF) data. The energy of this signal is rich in the information that can be used to perform the specific diagnosis task, e.g., lesion detection, lesion type discrimination, and so forth.

However, because of the carrier frequency included in the RF signal, the human eye-brain system cannot analyze the available task information efficiently when the RF data is directly displayed. Accordingly, the RF data is sent through a second stage that includes display processing. Conventionally, at the display stage, the envelope of the RF data is displayed, which is denoted as the B-mode image. The envelope of the RF data is mathematically calculated by summing intensity of the signal (signal squared) and the intensity of the 90-degree shifted version of the signal. Conceptually, the envelope of a modulated signal is a smooth curve outlining its extremes. Thus, calculating the envelope eliminates both carrier frequency and phase of the signal. The carrier frequency, as its name suggests, contains no diagnosis information. Losing the phase of the signal, however, raises questions whether or not the phase contains useful information regarding the specific diagnosis task. Studies and analysis of the phase signal over the past 30 years have not lead to extraction of any meaningful information.

The inventors re-investigate the problem of lost information due to envelope detection in ultrasound using a new information analysis approach. In this approach, energy of the ultrasound signals is analyzed to calculate the available task information. This analysis has revealed for the first time that the signal energy available in the RF data includes diagnostic information distributed over a spatial frequency spectrum which is made up of two lobes: a baseband lobe and a high-frequency lobe (with symmetric components on positive and negative spatial frequency axis). This spectrum describes the sensitivity of the RF data to task information available in the backscattering signal. Specifications of this spectrum are derived from ultrasound system and noise specifications.

The analysis of the B-mode data energy has further revealed that the energy of the B-mode image only contains a part of task information that is distributed over baseband lobe. This implies that the information collected through the high-frequency lobe in the RF data is not displayed in the B-mode image. In other words, the sensitivity of the B-mode image to the task information is limited to the baseband components. Moreover, the energy of the conventional B-mode image also does not contain all the task information of the baseband lobe. The inventors have further revealed that the information contained in the B-mode image can be improved if the RF data is pre-whitened using a Wiener filter before going through the display processing. In this case, the resulted B-mode image is referred to as prewhitened B-mode image. The processing that generates the prewhitened B-mode is analyzed to understand the improvement in transferring task information. The results show that the prewhitened B-mode processing does not transfer any task information distributed over the high-frequency lobe. However, in contrast to the conventional B-mode image, the prewhitened B-mode image contains all the task information distributed over the baseband lobe. Even for this improved case, the task information that is collectable in the prewhitened B-mode image is limited to approximately half the bandwidth, and thus the B-mode image may potentially lose a significant amount of diagnostic information.

The inventors found that the high-frequency information is lost in the summation of real and imaginary parts of the RF data intensity that lead to the envelope signal used to generate the B-mode image. With the insight gained from this analysis, the inventors developed a solution to recapture the information through calculating the difference between the summation terms and then losing the carrier frequency through demodulation. This solution is valuable not only because it brings back the lost information, but also because the solution does it through an efficient process of subtraction between previously available components. The inventors refer to the resulting image as a "complement image" because the complement image completes the transfer of information to the ultrasound display. In applications such as microcalcification detection where high-frequency information plays an important role, it is shown that using a complement image instead of (or combined with) the B-mode image enhances diagnostic performance.

While the present disclosure describes the present embodiments as applied to B-mode sonography, the present disclosure and embodiments may also be applied to other imaging such as A-mode, C-mode or M-mode imaging. Accordingly, while the present disclosure is explained with respect to B-mode imaging, one skilled in the art will appreciate that these embodiments may also be applied to other modes of sonographic imaging, and therefore, the scope of the disclosure is not limited to B-mode imaging.

Figure 4D:
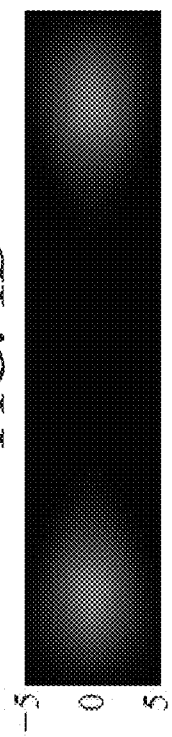
FIGS. 4A through 4E are images of a spectrum describing the sensitivity of the ultrasound processing to task information for an example ultrasonic pulse profile with the center frequency and percent bandwidth of 6.81 MHz and 56%, respectively, and represent sensitivity of the disclosed imagining system to task information transfers at different stages of ultrasonic imaging.
Figure 4E:
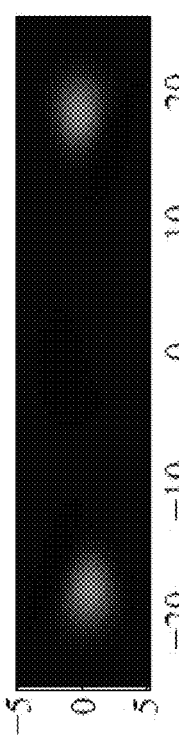
Figure 4A:
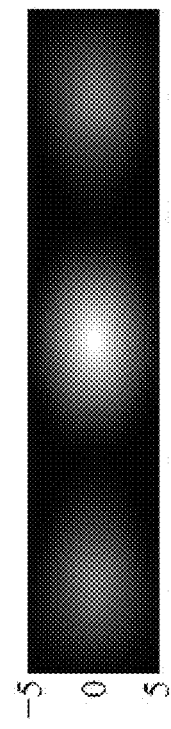
Figure 4B:
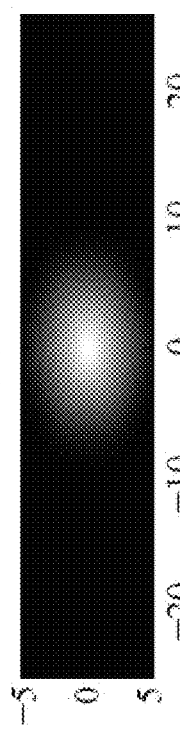
Figure 4C:
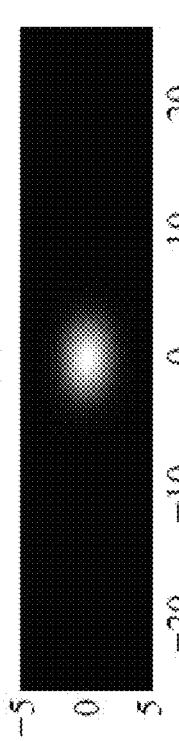

By way of example, FIGS. 4A through 4E illustrate spatial frequency domain channels for transfer of task information in an example ultrasonic imaging system. An ultrasound transducer pulse with the center frequency and percent bandwidth of 6.81 MHz and 56%, respectively, is considered. FIGS. 4A through 4E represent the sensitivity of this system to task information transfers at different stages of ultrasonic imaging process. The sensitivity is represented in the two-dimensional (2-D) spatial frequency domain where the axial and lateral spatial frequency axes denote the direction of ultrasound beam and the direction perpendicular to the ultrasound beam, respectively. Specifically: (a) FIG. 4A illustrates the sensitivity of the RF data processing to task information; (b) FIG. 4B illustrates the sensitivity of the prewhitened B-mode processing to task information; (c) FIG. 4C illustrates the sensitivity of the conventional (non-prewhitened) B-mode processing to task information; (d) FIG. 4D illustrates the sensitivity of prewhitened complement processing to task information; and (e) FIG. 4E illustrates the sensitivity of non-prewhitened complement processing to task information.

As FIGS. 4A, 4B and 4C illustrate, the task information spectrum at the acquisition stage includes one baseband lobe and high-frequency lobes. The B-mode imaging process transfers the task information contained in the baseband lobe to the display stage, but no task information spectral components within the high-frequency lobes are transferred or displayed in the B-mode images (FIGS. 4B and 4C) because of the envelope detection process. Moreover, the task information spectrum for the prewhitened B-mode data provide a broader spectral sensitivity in the spatial frequency domain compared to the conventional (non-prewhitened) B-mode channels.

The sensitivity of the complement image to the task information shown in FIGS. 4D and 4E suggests that the complement image retrieves the task information concentrated in the high-frequency lobes, which is not transmitted through conventional B-mode processing. It can be seen that the superposition of prewhitened B-mode and complement task information spectra shown in FIGS. 4B and 4D, respectively, is the same as the sensitivity of the RF data to task information (FIG. 4A).

Ultrasound Imaging Device Components

FIG. 1 is a diagram of an imaging device 100 according to one embodiment of the present disclosure. While these embodiments may apply to many types of imaging devices, the present disclosure is focused on an ultrasound machine capable of sonography for purposes of medical diagnosis. The imaging device 100 may include, but not be limited to, a probe 102 containing one or more transducer(s) 104 and an acoustic lens to steer emitted sound waves. The imaging device 100 may further include transducer pulse controls 109 to control amplitude, frequency and duration of pulses emitted from the transducers 104.

The imaging device 100 may further include a processing device 110, such as a central processing unit for computing, instruction execution and storage, and display management. The imaging device 100 may further include a disk storage device 115, a bus 120 or other type of communication channel, a display 130 and input/output (I/O) devices 140 such as a keyboard, cursor and a printer to print out a record of displayed data.

The probe 102 is the main part of an ultrasound machine. The probe 102 makes the sound waves and receives the echoes (also referred to herein as feedback or backscattering signal). The probe 102 generates and receives sound waves using a principle called the piezoelectric (pressure electricity) effect. In the probe, the transducers 104 include one or more quartz crystals called piezoelectric crystals. When an electric current is applied to these crystals, they change shape rapidly. These rapid shape changes, or vibrations, of the crystals produce sound waves that travel outward. Conversely, when sound or pressure waves hit the crystals, the crystals emit electrical currents. Therefore, the same crystals can be used to send and receive sound waves. The probe may also include a sound absorbing substance to eliminate back reflections from the probe itself, and the acoustic lens 108 to help focus the emitted sound waves.

Transducer probes 102 come in many shapes and sizes. The shape of the probe 102 determines its field of view, and the frequency of emitted sound waves determines how deep the sound waves penetrate and the resolution of the image. Transducer probes may contain one or more crystal elements (or transducers 104). In multiple element probes, each crystal may have its own circuit. Multiple element probes have the advantage that the ultrasonic beam can be "steered" by changing the timing in which each element gets pulsed, where steering the beam is more important for some imaging such as in cardiac ultrasound. In one embodiment, the steering capability enables using an angular compounding technique that takes frames at different angles around an area of interest of a patient or of a specimen (or phantom) in the disclosed experiments.

The processing device 110 is the brain of the imaging device 100 and may be or may include a type of central processing unit, system on a chip, integrated circuit, or the like. The processing device 110 may contain a microprocessor, memory, amplifiers and power supplies for the microprocessor and the probe 102. The processing device may send electrical currents to the probe 102 to emit sound waves, and also receive the electrical pulses from the probes that were created from the returning echoes. The processing device 110 may then perform the calculations involved in processing the data. Once the raw data are processed, the processing device 110 forms the image on the display 130, which may be any sort of monitor, liquid crystal display (LCD) or other type of display. The processing device 110 can also store the processed data and/or images on the disk storage device 115 for later retrieval.

During operation of the imaging device 100, whenever a sound wave encounters a material with a different density (acoustical impedance), part of the sound wave is reflected back to the probe and is detected as an echo (or feedback signal). The time it takes for the echo to travel back to the probe is measured and used to calculate the depth of the tissue interface causing the echo. The greater the difference between acoustic impedances, the larger the echo is.

If the pulse hits gases or solids, the density difference is so great that most of the acoustic energy is reflected and it becomes impossible to see deeper. The frequencies used for medical imaging are generally in the range of 1 to 18 MHz. Higher frequencies have a correspondingly smaller wavelength, and can be used to make sonograms with smaller details. However, the attenuation of the sound wave is increased at higher frequencies, so in order to have better penetration of deeper tissues, a lower frequency (3-5 MHz) may be used.

Seeing deep into the body with sonography is very difficult. Some acoustic energy is lost every time an echo is formed, but most of what is lost is lost from acoustic absorption. The speed of sound varies as it travels through different materials, and is dependent on the acoustical impedance of the material. The sonographic instrument, however, assumes that the acoustic velocity is constant at 1540 m/s. An effect of this assumption is that in a real body with non-uniform tissues, the acoustic beam becomes somewhat defocused and image resolution is reduced.

To generate a two-dimensional (2D) image, the ultrasonic beam is swept. A transducer may be swept mechanically by rotating or swinging. Or, a one-dimensional phased array transducer may be used to sweep the beam electronically. The received data may be processed and used to construct the image. The image is then a 2D representation of the slice into the body.

Three dimensional (3D) images can be generated by acquiring a series of adjacent 2D images. A specialized probe that mechanically scans a conventional 2D image transducer may be used to generate a 3D image. Since the mechanical scanning is slow, however, it is difficult to make 3D images of moving tissues. Recently, 2D phased array transducers that can sweep the beam in 3D have been developed. These can image faster and can even be used to make live 3D images of a beating heart.

Stages of Modified Ultrasound Device Components

Figure 2:
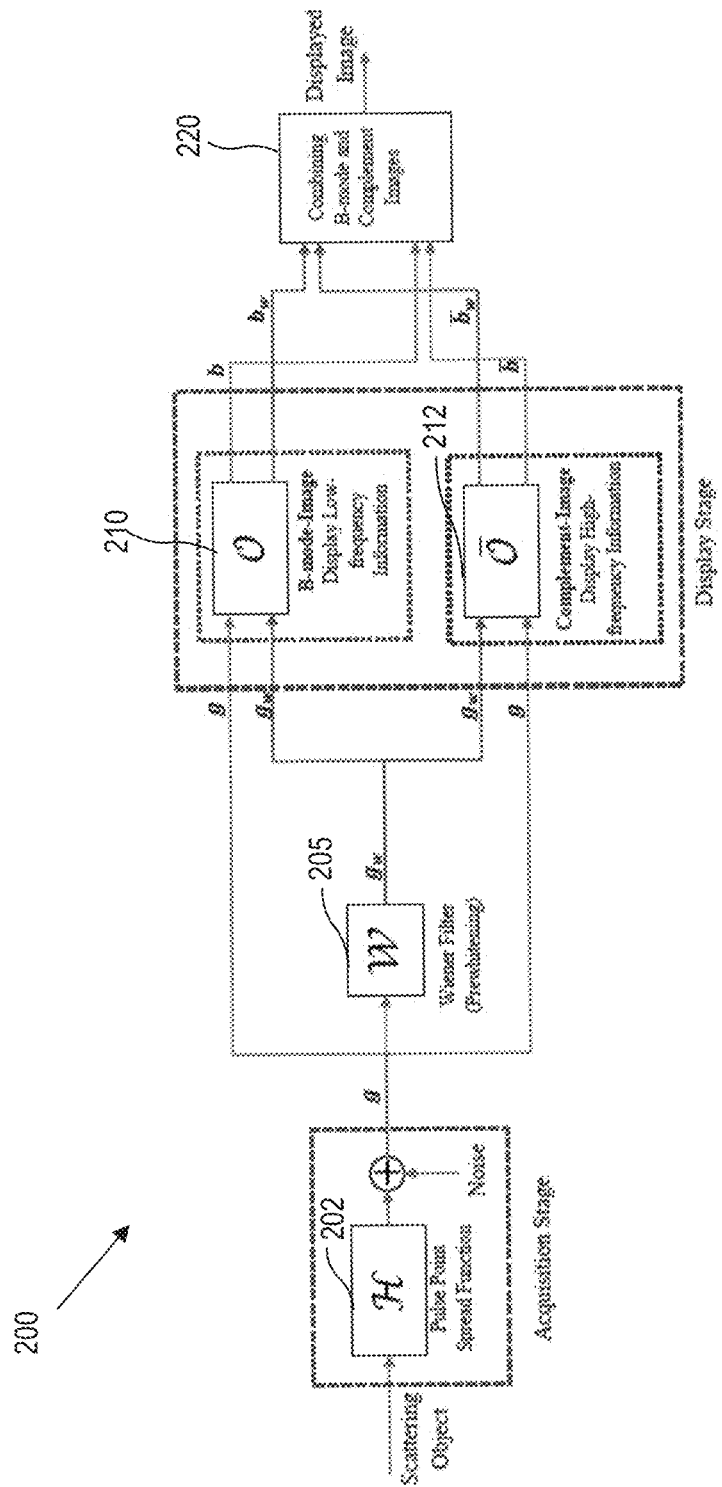
FIG. 2 is a diagram of a system model of sonographic data processing according to an embodiment of the present disclosure.

FIG. 2 is a diagram of a system model 200 of sonographic data processing according to an embodiment of the present disclosure. The processing device 110 may acquire and display an image during sonographic operation in three stages. In a first, or acquisition stage, the echo or feedback signal is captured with a transform filter 202, which may also add in some noise from unwanted wave reflections during RF data generation. The captured feedback signal includes radio-frequency (RF) data within a carrier signal from which an image suitable for diagnosis is extracted. In an optional pre-processing step, the processing device 110 may perform prewhitening filtration with, for example, a Wiener filter 205 in order to filter out some of the noise added in during the RF data acquisition.

The second stage is referred to as the display stage, in which the processing device 110 processes the captured RF data. Display stage processing in ultrasonic image formation increases the accessibility of some diagnostic information for human observers, even if it can lower the total information content of the display relative to the recorded echo signals. This stage includes different processing such as demodulation, mixing, downsampling, gray-scale mapping, etc. Conventionally, the main processing at this stage performs envelope detection or demodulation. A primary purpose of demodulation is to filter out the carrier signal and reduce the frequency to a frequency suitable for image generation. This second stage may be designed to map task information embedded in the variance of the RF data into a demodulated low-frequency image.

The processing device 110 may perform B-mode image generation 210 (or other sonographic mode image generation) in a portion of the display stage to capture low spatial frequency information in the RF data. While the B-mode image is conventionally the main output of ultrasound display stage processing, the inventors have added a complement imaging component 212 to generate the complement image in another portion of the display stage, to capture high spatial frequency information in the RF data.

The conventional B-mode image is created using a non-linear operator, $b=\mathcal{O}\{g\}$, where g and b represent the RF data and B-mode data, respectively. While $\mathcal{O}$ represents the various processing mentioned earlier, in this disclosure, the most basic representation of the B-mode processing is considered, which is the demodulation of the RF data, g•Hence, the B-mode data vector is represented as $$b=|g_+| \qquad (1)$$

where $g_+$ denotes the analytical signal representation of RF data, g, the absolute value of which demodulates the RF data and generates B-mode image, b. Alternatively, B-mode intensity $b^2$ can be represented as the summation of the RF data intensity $g^2$ and the RF Hilbert transform intensity $\hat{g}^2$ as $$b^2=g^2+\hat{g}^2 \qquad (2)$$

The Hilbert transform is a linear filter that calculates the 90-degree rotation of the input signal g, which represents the imaginary part of the RF data. We can also define prewhitened B-mode data, $b_w$, which is derived from the Wiener-filtered RF data as $$b_w=\mathcal{O}\{g_w\}. \qquad (2)$$

Figure 3A:
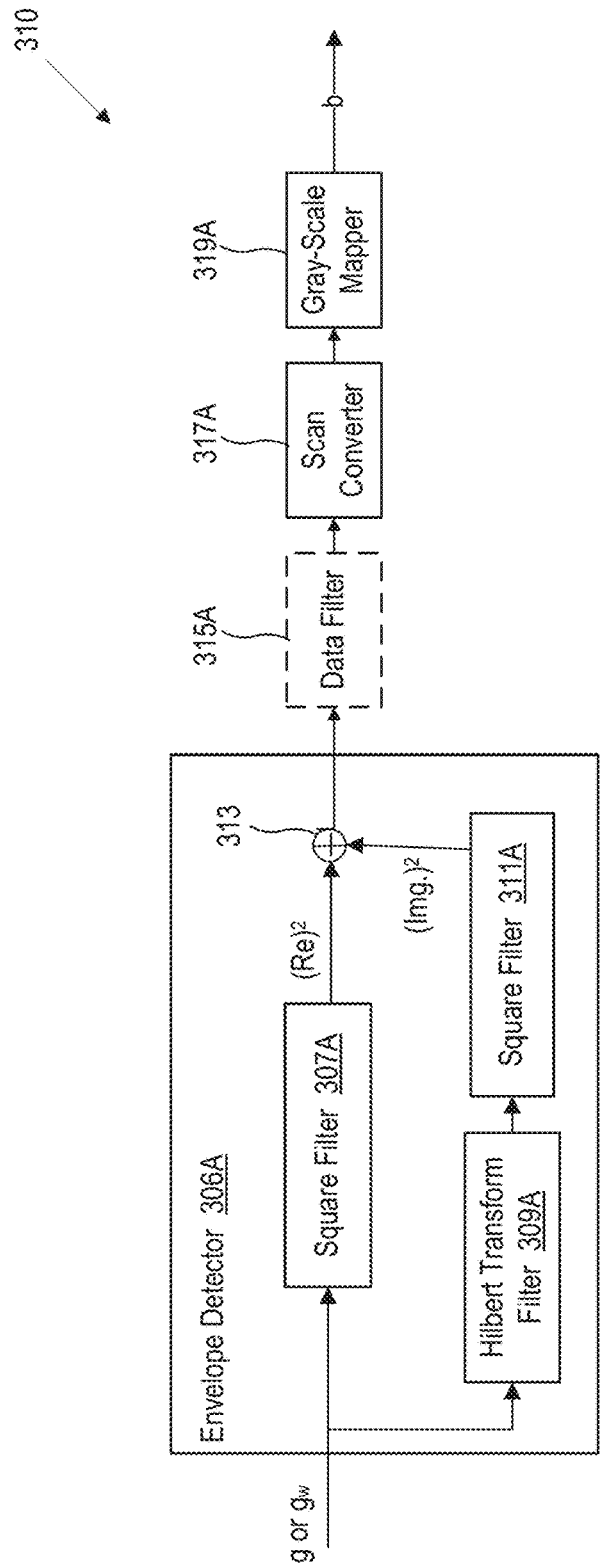
FIG. 3A is a diagram of a series of brightness (B)-mode imaging components according to one embodiment of the present disclosure.

FIG. 3A is a diagram of a series of brightness (B)-mode imaging components 310 according to one embodiment of the present disclosure that may be used to demodulate the RF data signal that resulted from the acquisition stage of FIG. 2 (which may or may not be whitened). These components may include, but not be limited to an envelope detector 306A to detect and output an envelope signal, an optional data filter 315A, a scan converter 317A and a gray-scale mapper 319A, the output of which is a B-mode image suitable for display as an image.

The envelope detector 306A may further include a first square filter 307A that calculates the square of the real part of the RF data signal. The envelope detector 306A may further include a Hilbert transform filter 309A that generates the imaginary part of the RF data signal, and a second square filter 311A that calculates the square of the imaginary part of the RF data. The envelope detector 306A may further include a summer 313 to add the square of real part and the square of the imaginary part of the RF data signal, and output a B-mode envelope signal. The envelope detector 306A may remove the frequency and phase of the feedback signal in generating the B-mode envelope signal.

The data filter 315A, if present, may filter out any noise components from the B-mode envelope signal that are outside the signal band. The scan converter 317A may down sample the filtered envelope signal and convert the envelope of the RF data signal intensity to an image. The gray-scale mapper 319A may map the image in gray scale suitable for display as, for example, a B-mode image used for diagnosis.

Let's introduce the complement image, $\bar{b}$ based on the difference between the square of the real part and the square of the imaginary part of the RF data as $$\bar{b}^2=g^2-\hat{g}^2. \qquad (3)$$

Figure 3B:
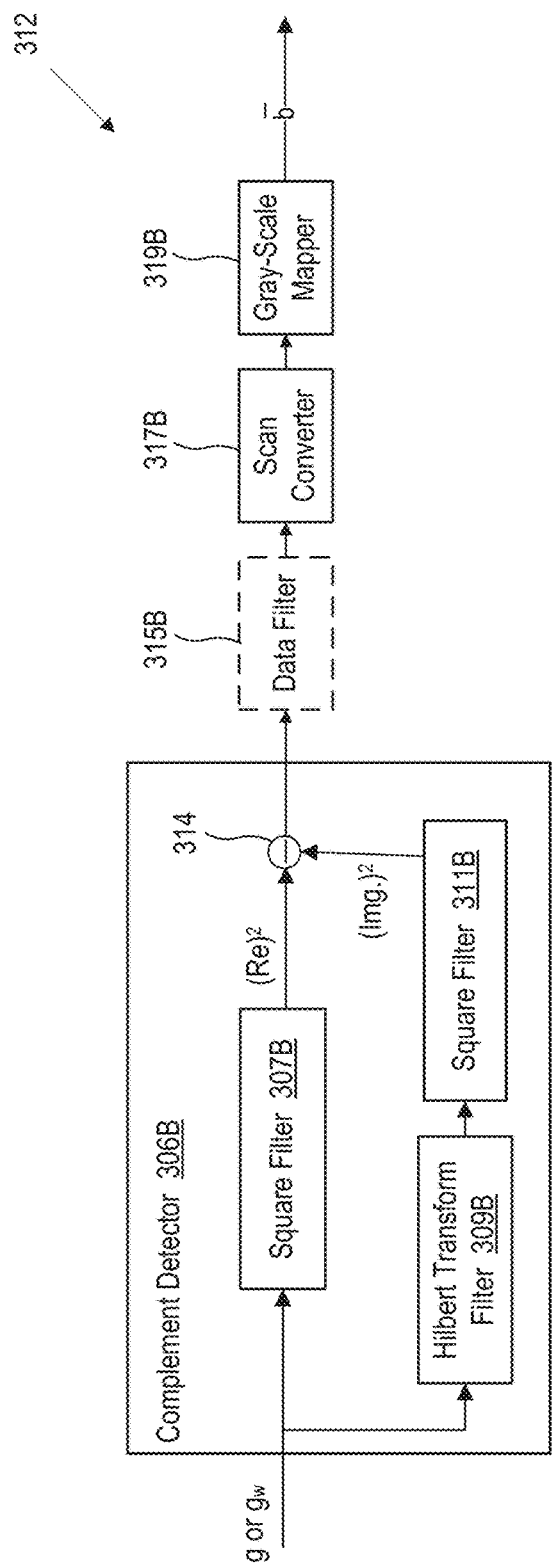
FIG. 3B includes a diagram of a series of complement imagining components according to an embodiment of the present disclosure.

FIG. 3B includes a diagram of a series of complement imagining components 312 according to an embodiment of the present disclosure that is applied on the RF data signal resulting from the acquisition stage of FIG. 2. These components may include, but not be limited to, a complement detector 306B to detect and output a complement signal, an optional data filter 315B, a scan converter 317B and a gray-scale mapper 319B, the output of which is a complement image suitable for display.

The complement detector 306B may further include a first square filter 307B that calculates the square of the real part of the RF data signal. The complement detector 306B may further include a Hilbert transform filter 309B that calculates the imaginary part of the RF data signal, and a second square filter 311B that calculates the square of the imaginary part of the RF data. The complement detector 306B may further include a subtractor 314.

Different from the image generation of FIG. 3A, the subtractor 314 of FIG. 3B subtracts the square of the imaginary part of the RF data from the square of the real part of the RF data. These components are already available in the B-mode image generation, and thus after performing a Hilbert transform, the complement imaging components 312 may generate a complement image that recovers high frequency information available in the RF data that would be lost if generating only the B-mode image. Accordingly, in one embodiment, the square filter 307A and the square filter 307B are the same filter, the Hilbert transform filter 309A and the Hilbert transform filter 309B are the same filter, and the square filter 311A and the square filter 311B are the same filter.

With further reference to FIG. 2, a third (or combination) stage 220 may be included in order to combine the B-mode (or other mode) image with the complement image, either as two separate images or with the complement image as an overlay on top of the B-mode image. To overlay the complement image on top of the B-mode image, first an intensity threshold may be applied on the complement image to filter out its brighter intensity spots. Those spots represent the locations in the image that contain high-frequency task information. The inventors refer to this process as thresholding. The output of the thresholding may be color-coded and overlaid over the top of the gray-scale B-mode image. The B-mode image, the complement image and/or the combined image of the B-mode and the complement image may be displayed on the display 130 and optionally stored in the disk storage device 115.

The task information transfer from the acquisition stage to the display stage can be theoretically perfect if the RF data is prewhitened and both B-mode and complement data are combined at the display stage output. Note that the above discussion relates to the efficiency of transferring task information throughout the imaging stages. The present disclosure does not discuss the task information of the backscattering signal that could be lost in the acquisition process. Achieving perfect efficiency using complement image is a theoretical result. An ideal B-mode process is considered here where the display-stage filters do not introduce any noise to the signal. Also, if the pulse profile of the ultrasound system is not known, Wiener filtering may only be approximate. Efficiencies less than one could be achieved if these conditions are not ideal.

Results

In a practical application covered in this disclosure, an ultrasonic imaging system is considered which aims to provide the visual information required for diagnosing breast disease. We are interested in discriminating lesions of two possible classes: malignant (hypothesis $H_1$) and benign (hypothesis $H_0$). Images of each class will differ in features of the ensemble statistical profile, which is reflected in the backscatter signal statistics.

We consider a typical pulse profile with the center frequency and percent bandwidth of 6.81 MHz and 56%, respectively, and echo signal-to-noise ratio (SNR) of 30 dB. To illustrate the ability of the complement image to transfer high spatial frequency task information from the RF echo signal into image, we designed a simulation scenario using an artificial wide-spectrum scattering object. We consider a zero-mean Gaussian distributed scattering object as in a covariance function for f, characterized by a spatially modulated variance, which resembles a wide-spectrum chirp pulse. The linear chirp spectrum sweeps spatial frequencies along the horizontal axial dimension within the Nyquist rate, namely from 0 $mm^{-1}$ up to 25 $mm^{-1}$ for the disclosed imaging device. A linear-chirp variance is of interest because axial locations on the variance profile are linearly mapped into specific spatial frequencies. The chirp object, which is a realization of this statistical model, is scanned by the imaging system and processed into prewhitened and non-prewhitened B-mode and complement images. The sensitivity of each of these processes as a function of axial-spatial frequency can be determined by observing the visible parts of the chirp pulse in each of the images.

Figure 5:
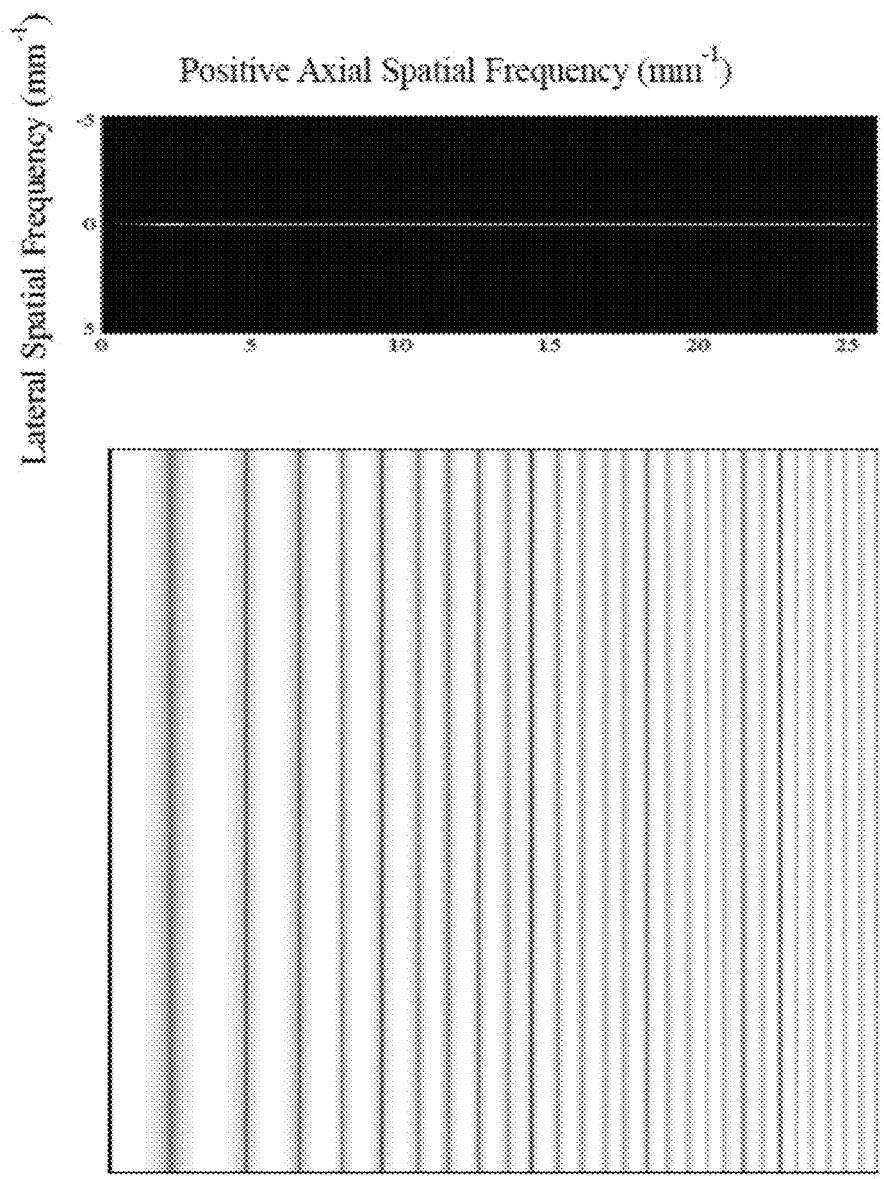
FIG. 5 is an image of a chirp task used to test the disclosed B-mode and complement imaging as well as the spatial frequency representation of this task.
Figures 5A, 5B:
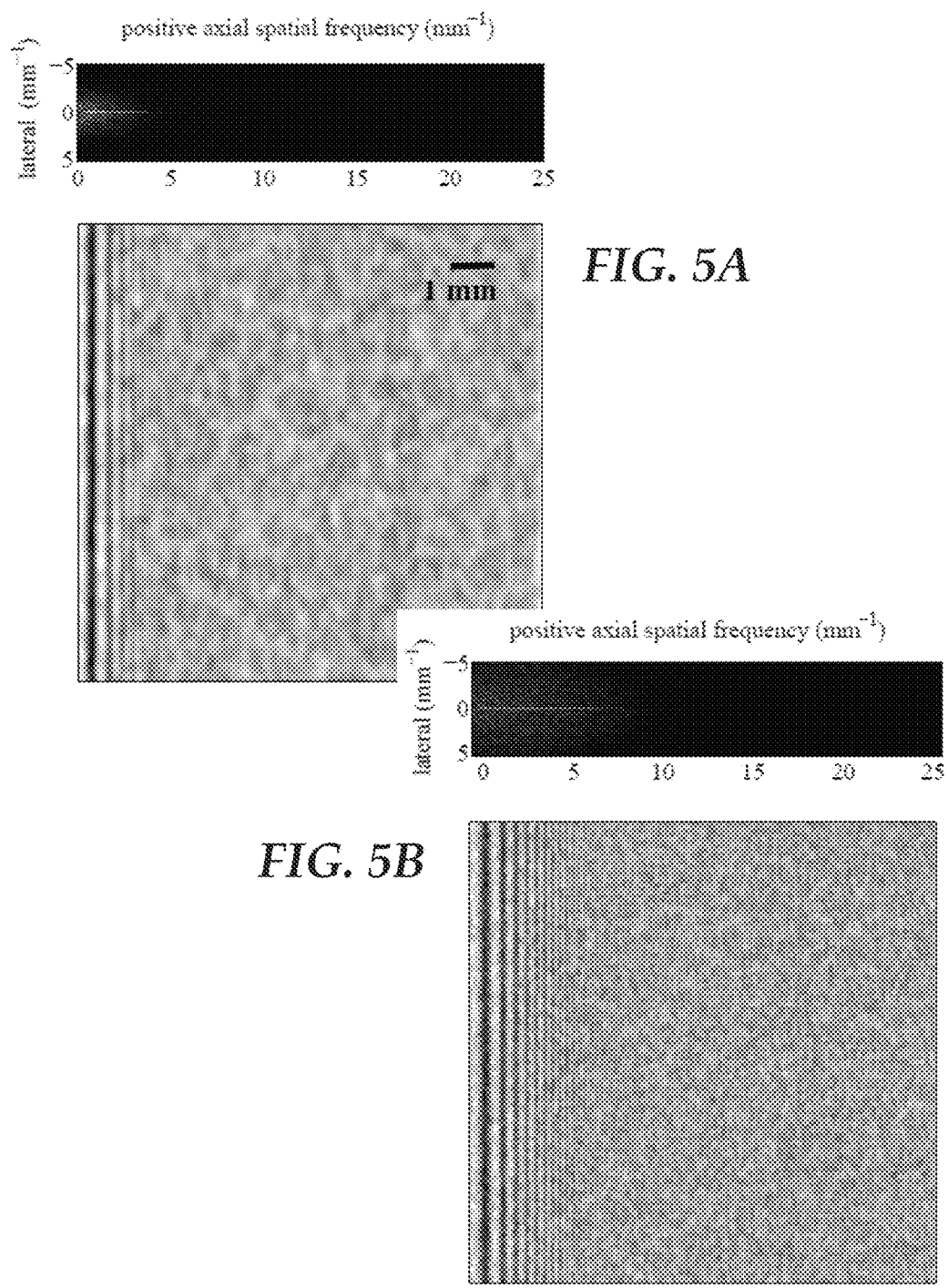
FIG. 5A is an image of a B-mode data spectrum (top) and a B-mode image (bottom) of an ultrasonic display of the chirp task.
FIG. 5B is an image of a B-mode data spectrum (top) and a prewhitened B-mode image (bottom) of an ultrasonic display of a chirp task.

FIG. 5 is an image of a chirp task used to test the disclosed B-mode and complement imaging. FIGS. 5A, 5B and FIGS. 5C, 5D illustrate the B-mode and complement images for the chirp task, respectively. The B-mode process transfers the initial part of the low-frequency components of the chirp pulse. This can also be observed from the frequency domain representation of the B-mode image also illustrated in FIGS. 5A and 5B. The spectral sensitivity range for the prewhitened B-mode data (FIG. 5B) is considerably broader in the frequency domain compared to the non-prewhitened B-mode data (FIG. 5A). This effect can be explained by considering the de-correlating property of the Wiener filter, which results in finer speckle correlation cells. Smaller correlation cells make is possible to resolve higher chirp frequencies.

The complement images generated from the chirp task are expected to display high-frequency parts of the task. The high-frequency components are not well matched with the human observer eye-brain system. Thus, the processing device 110 eliminates the carrier in the complement images and displays the baseband equivalent representation of the complement image, $\bar{b}_{BB}$, denoted as baseband complement image. Because complement images do not contain low-frequency components (see FIGS. 4D and 4E), eliminating the carrier can be achieved by envelope detection without losing any information.

Figures 5C, 5D:
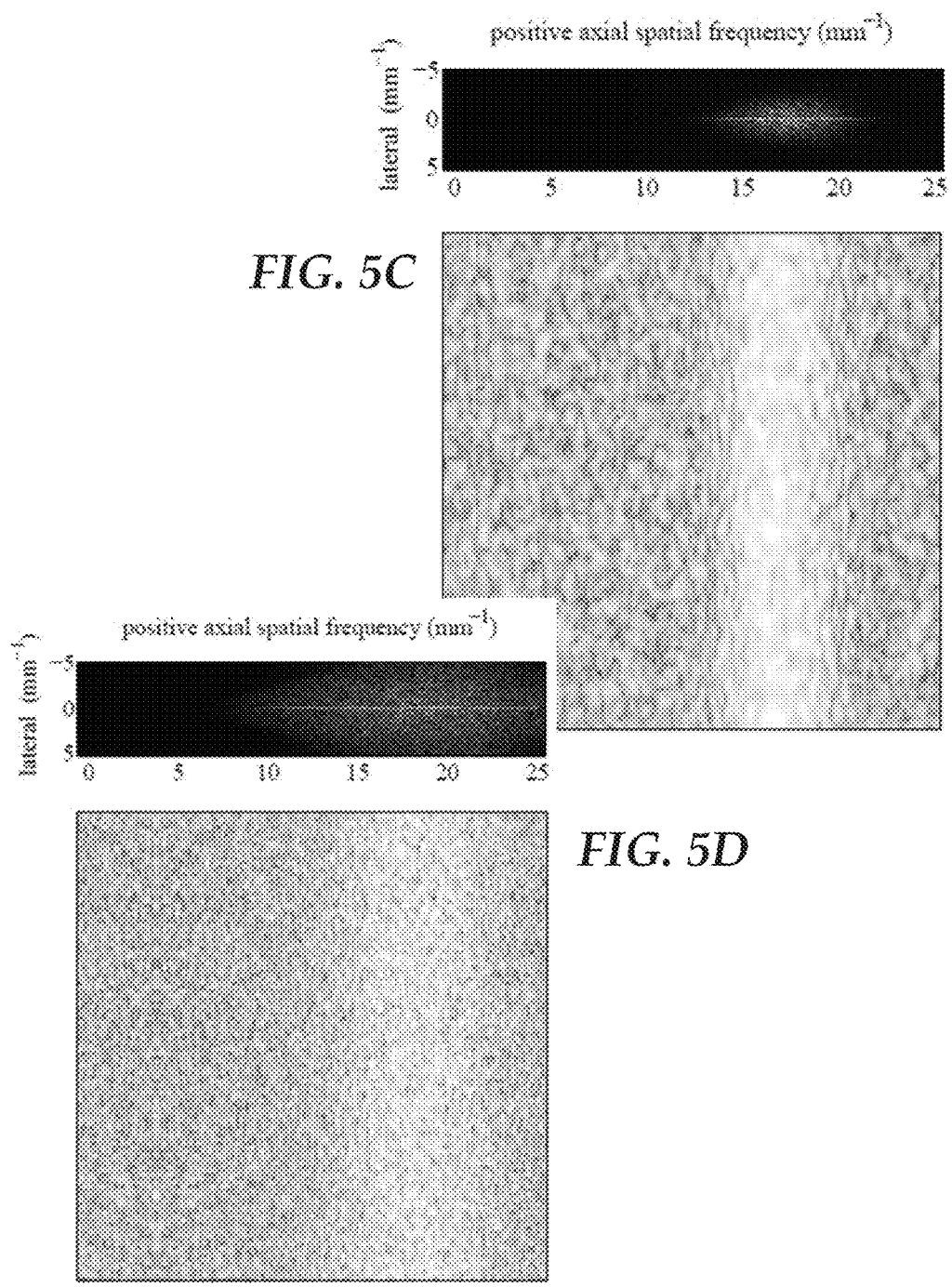
FIG. 5C is an image of a complement data spectrum (top) and a baseband complement image (bottom) of an ultrasonic display of a chirp task.
FIG. 5D is an image of a prewhitened, complement data spectrum (top) and a prewhitened baseband complement image (bottom) of an ultrasonic display of a chirp task.

The baseband complement images for the chirp task are also illustrated in FIGS. 5C and 5D. Complement images display bright strips associated with the high-frequency chirp components. While the exact frequency information is not displayed in the baseband complement images, the location(s) of bright spot(s) specify the existence of high-frequency task energy. For many applications like edge-detection and small particle detection, locating high-frequency components contains important clinical information for diagnostic purposes by indicating the existence of rough edges or small particles at those locations. FIGS. 4B and 4D also illustrate that the prewhitened complement image transfers a wider spectrum range compared to the non-prewhitened complement image, which can be explained by the de-correlating and whitening effect of Wiener filter.

Application in Detecting Microcalcifications

A combination of B-mode and complement data can transfer spatial frequencies of task information in the entire RF echo spectrum bandwidth into the display stage. Using the complement image may provide more value for tasks with energy contained in the higher frequency components. Boundary discrimination tasks and other small-area tasks are among such cases. Small-area tasks are diagnosis tasks where the difference of area for hypothesis 1 and 0 is small compared to the ultrasound pulse area. Detecting microcalcifications in a breast lesion to discriminate malignant and benign lesions is one example of high-contrast small-area tasks.

Figure 6A:
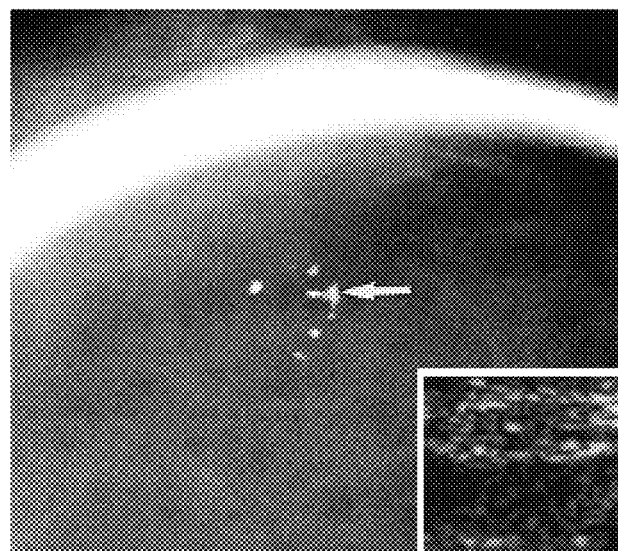
FIG. 6A is an 11 mm breast mammography image with an about 4 mm clustered microcalcification.
Figure 6B:
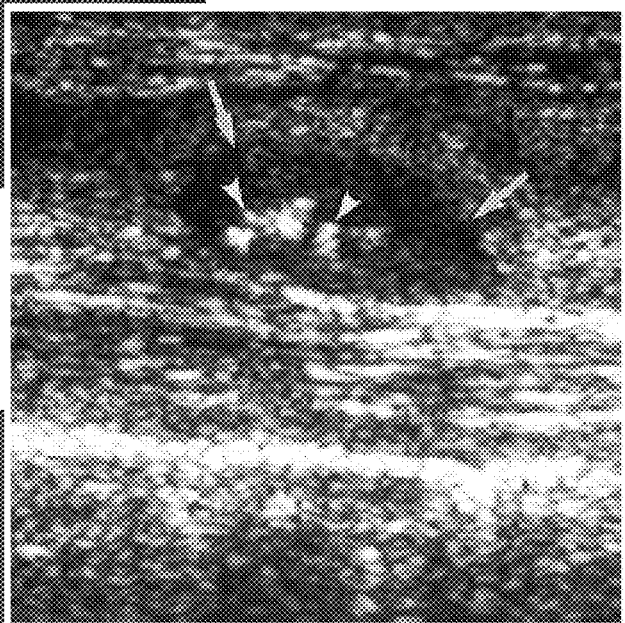
FIG. 6B is an 11 mm ultrasound B-mode image of the same area for the same patient as the 11 mm breast mammography image of FIG. 6A.
Figure 6C:
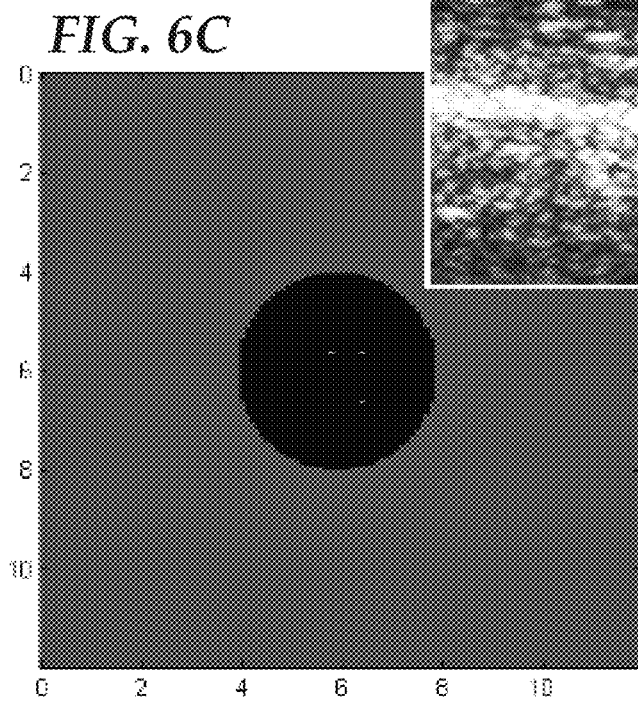
FIG. 6C is a 12 mm phantom image with a 4 mm diameter, hypo-echoic lesion with simulated microcalcifications.

FIGS. 6A, 6B and 6C illustrate clinical examples of microcalcification detection using a mammogram and B-mode imaging. The mammogram in FIG. 6A clearly depicts the number and positions of microcalcifications. For the B-mode image of FIG. 6B, however, while the calcified cluster is shown as a bright spot because of the high contrast of inclusions, the microcalcifications cannot be unambiguously identified. The reason is that these small but highly scattering particles introduce high-frequency components to the task that are not transferred through the conventional B-mode image formation process.

To study the potential effectiveness of complement images, we consider the task of detecting microcalcifications inside a 4 mm breast lesion, which approximately resembles the real-world case in FIG. 6B. Under the null hypothesis, no inclusions are present inside the lesion. The alternative hypothesis, shown in FIG. 6C, represents the case where the lesion contains three 50 µm calcium inclusions with a very high contrast (10 times the background variance) to model the strong scattering from microcalcifications.

Figure 7:
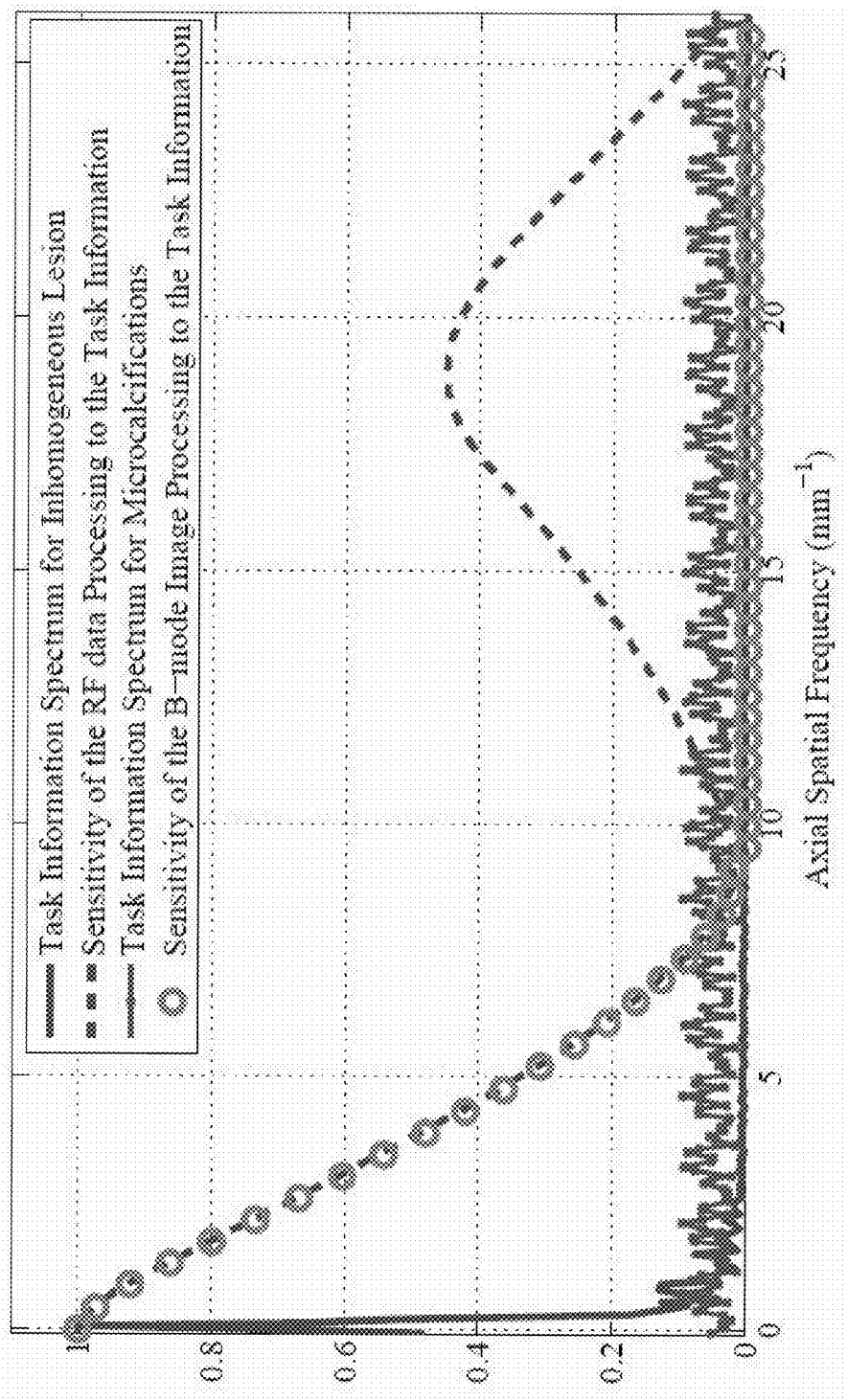
FIG. 7 is a one-dimensional (1-D) cross-section of an information sensitivity spectrum for RF data processing and B-mode processing, and depicts an information spectrum for a calcified inhomogeneous breast lesion.

The spectral properties of the information content for the microcalcification task are well illustrated in FIG. 7 where 1-D cross-sections of the 2-D Fourier transform of the task information is shown along the axial spatial frequency axis. The task information is separated into two parts namely the information associated with the microcalcifications and background lesion. As expected, the information associated with the microcalcifications is spread over the axial spatial frequency while the information associated with the background is mostly baseband information. The task information spectra are mapped over the spectra describing the sensitivity of RF, B-mode and complement image processing to the input information. These spectra are 1-D representations of the 2-D spectra in FIGS. 4A and 4B and 4D.

FIGS. 8A through 8F illustrate the simulated B-mode and complement images for this task (calcified breast lesion) when microcalcifications are present. The prewhitened (e.g., with a Wiener filter) of and non-prewhitened B-mode images of illustrate the large-area lesion with a higher contrast compared to the complement images. In the prewhitened B-mode image of FIG. 8D, lesion-boundary areas and some of the microcalcifications are less ambiguously displayed. However, the blurred display of microcalcifications in the B-mode images makes it unlikely to distinguish microcalcifications from other speckle spots in the image.

Figure 8C:
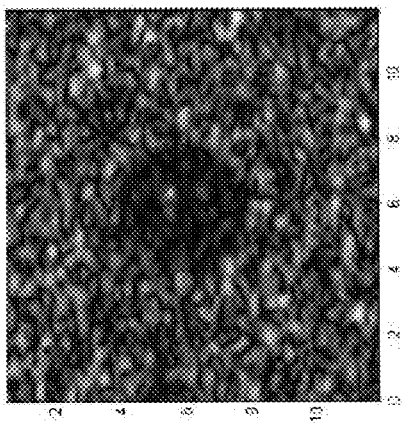
FIGS. 8A, 8B and 8C are images of an example non-prewhitened feedback signal for, respectively: (A) B-mode; (B) complement; and (C) a combination of B-mode and complement.
Figure 8F:
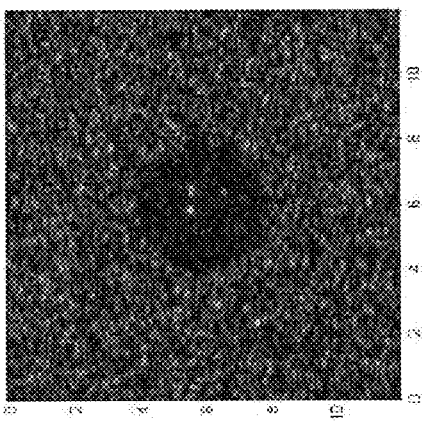
FIGS. 8D, 8E and 8F are images of an example prewhitened feedback signal for, respectively: (D) B-mode; (E) complement; and (F) a combination of B-mode and complement.
Figure 8B:
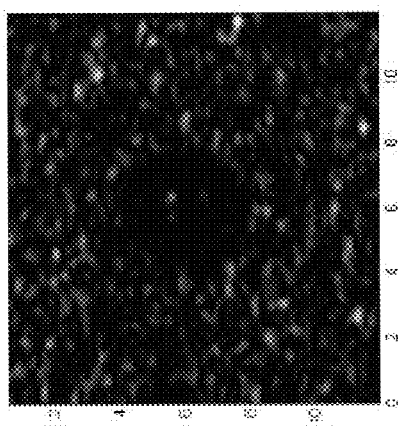
Figure 8E:
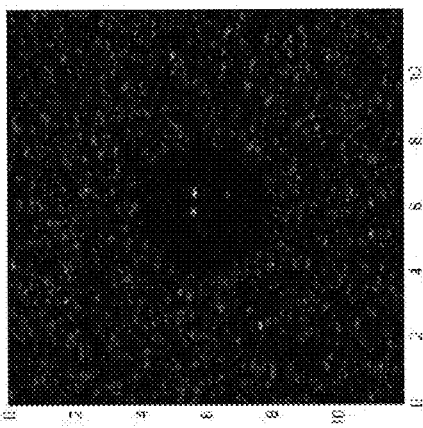
Figure 8A:
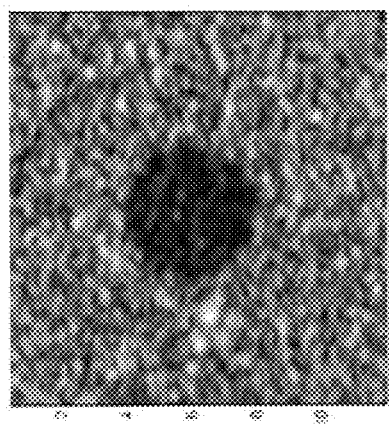
Figure 8D:
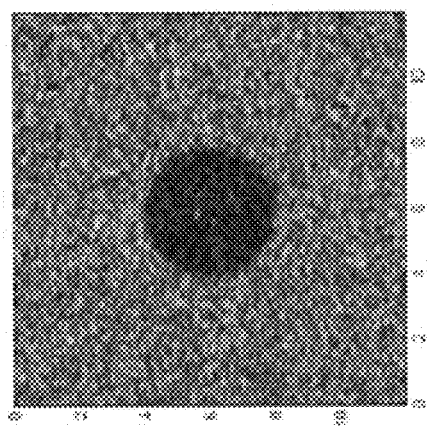

On the other hand, both prewhitened and non-prewhitened complement images (FIGS. 8B and 8E, respectively) depict microcalcifications with more clarity than the B-mode image. The distinction is better for the prewhitened complement image as it provides higher bandwidth for transmitting task spectrum (FIG. 7B). As FIGS. 8B and 8E illustrate, microcalcifications are displayed as high-contrast particles. Accordingly, the microcalcifications can be filtered out and selected by thresholding the complement images. FIGS. 8C and 8F illustrate the filtered complement images superimposed over gray-scale B-mode images with a different color-map to generate combined display outputs. While thresholding the non-prewhitened complement images results in a few false-alarm spots in the combined image, the prewhitened complement image has distinguished all three microcalcification spots in the image.

Comparison of different images in FIGS. 8A through 8F indicates that complement images can display the microcalcifications more effectively compared to B-mode images. The sensitivity of the complement image to high frequency task components explains this result. This is while background lesion information is best transferred through B-mode images because of their low frequency nature. To take complete advantage of the information transferred through each of these images, however, the processing device 110 may combine the low-frequency and high-frequency resultant images by superimposing the complement image over the B-mode image. Note that best detection performance is achieved for prewhitened complement image. However, in situations where pulse profile h is unknown, so prewhitening the data is not ideal, the complement image can still add high-frequency information to enable the detection of microcalcifications.

Application in Detecting Microcalcifications in Inhomogeneous Calcified Breast Lesion A relevant application of the present disclosure is that of a phantom where there exists both baseband and high-frequency information, such as an inhomogeneous breast lesion with small microcalcification inclusions. The detection of small calcified inclusions using ultrasound B-mode images is especially challenging in the presence of inhomogeneities in the lesion background that makes their distinction from microcalcifications difficult and sometimes impossible. This is where a complement image helps to distinguish hard-boundary micrometer inclusions by enhancing such inclusions in contrast to the soft boundary larger background inhomogeneities. Simulation results indicate excellent improved images from adding in the complement image, especially when Wiener filtering is used to prewhiten the data before it goes through the display processing stage.

Figure 9:
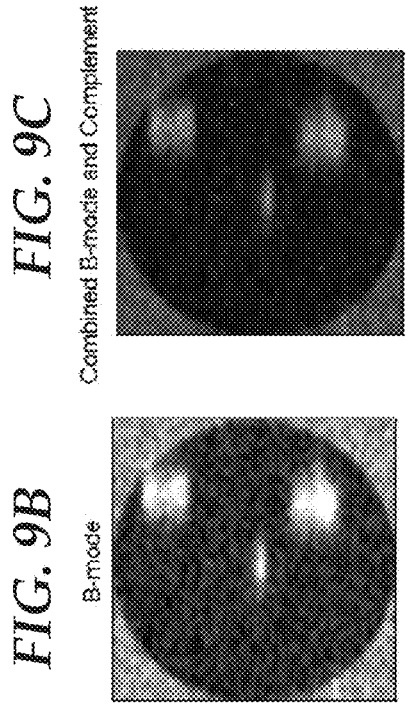
FIG. 9 is a phantom image of gelatin-based, phantom breast lesion used to generate simulation results.
Figure 9:
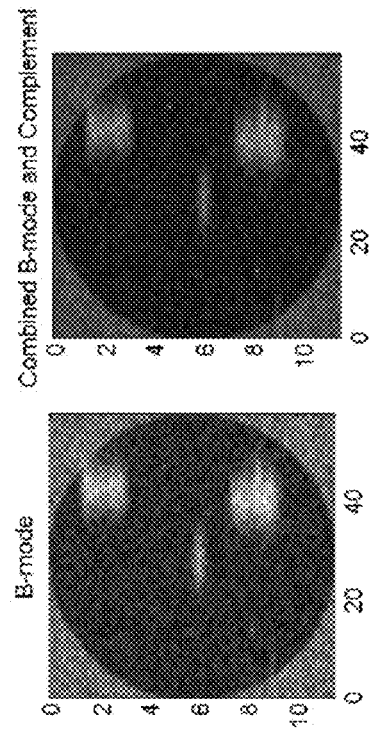
Figure 9:
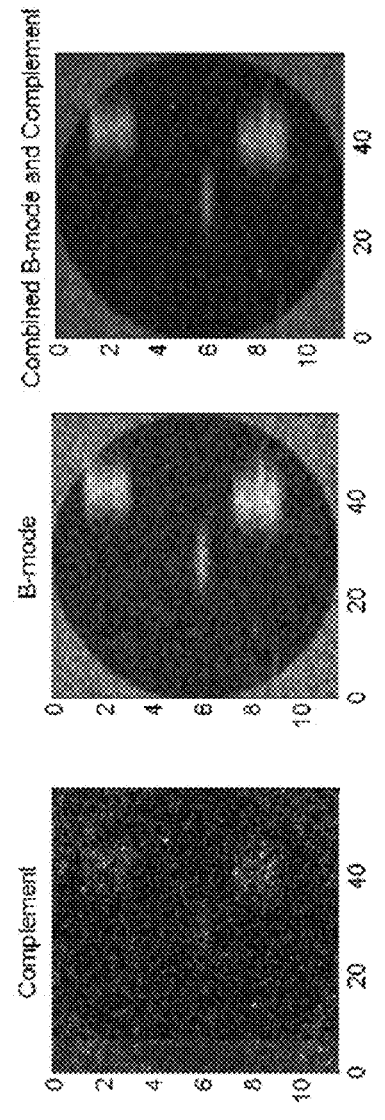
Figure 9:
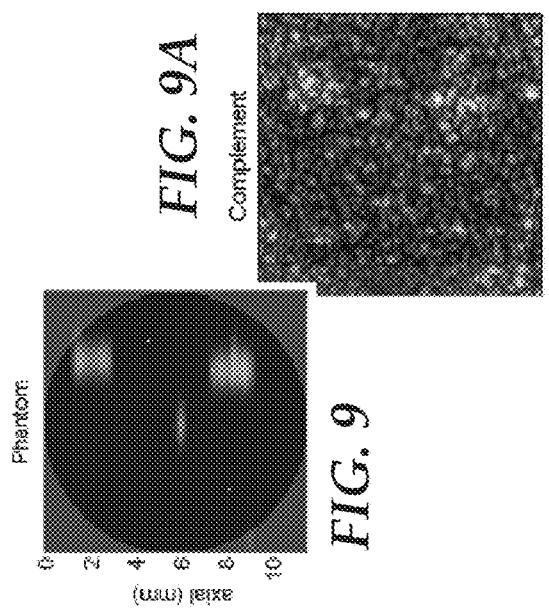

FIG. 9 is an image of breast lesion phantom used to generate simulation results. FIGS. 9A, 9B and 9C are images of a non-prewhitened feedback signal for the phantom breast lesion of FIG. 9, respectively: (A) complement; (B) B-mode; and (C) a combination of complement and B-mode. FIGS. 9D, 9E and 9F are images of a prewhitened feedback signal for the phantom breast lesion of FIG. 9, respectively: (D) complement; (E) B-mode; and (F) a combination of complement and B-mode. Note the ability to distinguish the microcalcifications within the complement image (particularly the prewhitened complement image) where the microcalcifications are almost imperceptible in the B-mode images.

Lab Measurement Results

Figure 10A:
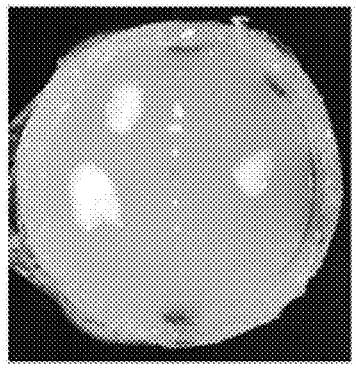
FIG. 10A is an image of a cross section of a gelatin phantom made in a lab.
Figure 10B:
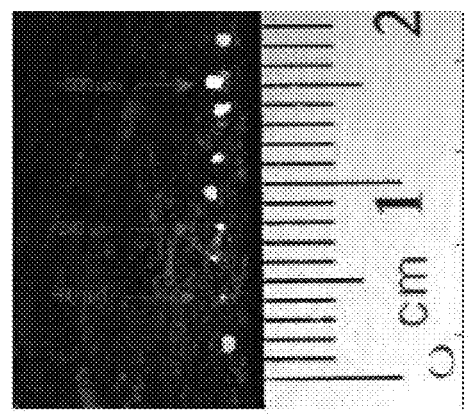
FIG. 10B is an image showing inclusions besides a ruler to provide an estimate of their diameter.

Next, the inventors tested the enhancement of diagnostic imaging by applying the complement imaging technique to lab generated phantoms. The inventors created a gelatin-based phantom with micrometer inclusions to mimic the microcalcifications and high-intensity scattering areas to mimic the background inhomogeneities. FIG. 10A is an image of a cross section of the gelatin phantom made in a lab. This phantom includes 15% gelatin background with 1% corn-starch scatting. Nine micrometer-sized inclusions made of chalk (calcium carbonate) are included along the center and periphery of the phantom. Three high-scattering corn-starch clumps made of gelatin and a high percentage of corn starch mimic inhomogeneity areas. FIG. 10B is an image showing microcalcification inclusions of FIG. 10A besides a ruler to provide an estimate of their diameter.

Figure 11C:
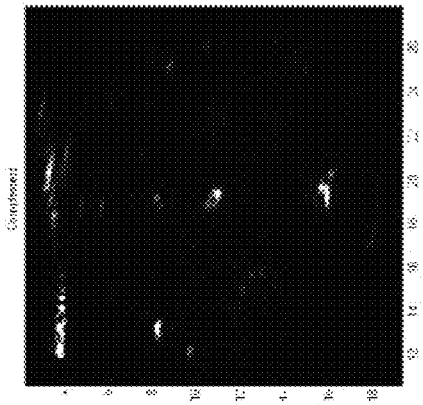
FIGS. 11A, 11B and 11C are images of a feedback signal using a Siemens® Antares Ultrasound machines, using VF 13-5 transduction at a nominal central frequency of 7.27 MHz and with a linear scale, respectively: (A) phantom lesion; (B) B-mode; and (C) complement.
Figure 11B:
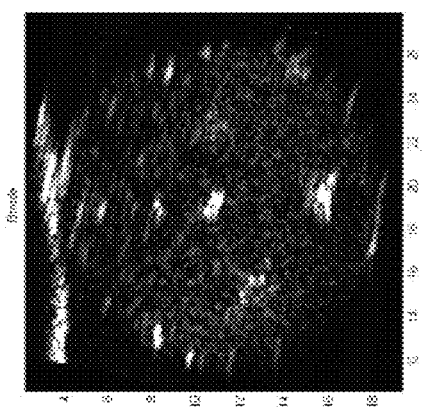
Figure 11A:
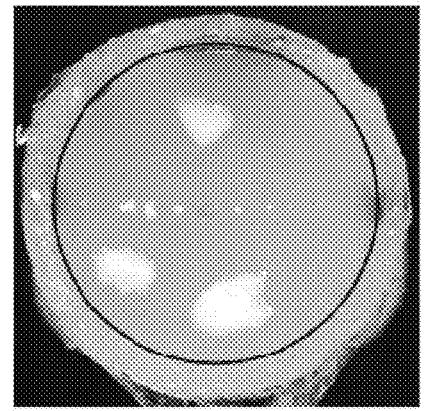

FIGS. 11A, 11B and 11C are images of a feedback signal using a Siemens® Antares Ultrasound machines, using VF 13-5 transducer operating at a nominal central frequency of 7.27 MHz, respectively: (A) phantom lesion; (B) B-mode image; and (C) complement image. Images are displayed with a linear scale. The B-mode image only shows the bigger inclusions along with traces of the three inhomogeneity areas. This is expected because the ultrasonic information associated with larger particles is mostly concentrated in baseband spatial frequency. The ultrasonic information associated with smaller particles has more significant high-frequency components that lie within the high spatial frequency bands. Thus, the complement image enhances the contrast between large inhomogeneities and small inclusions, making micrometer inclusions more detectable. The total energy of the signal collected in the baseband is more than that of high spatial frequency energy, making the B-mode image brighter than the complement image with the identical gray scale map.

Figure 12C:
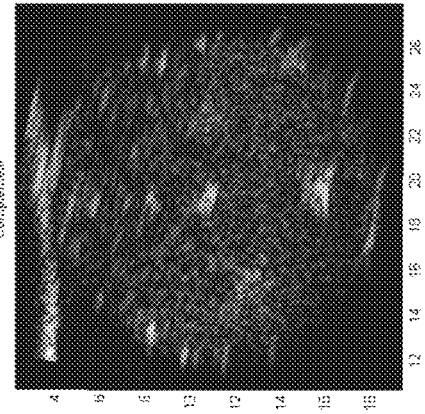
FIGS. 12A, 12B and 12C are images of a feedback signal using a Siemens® Antares Ultrasound machines, using VF 13-5 transduction at a nominal central frequency of 7.27 MHz and with a non-linear scale, respectively: (A) phantom lesion; (B) B-mode; and (C) complement.
Figure 12B:
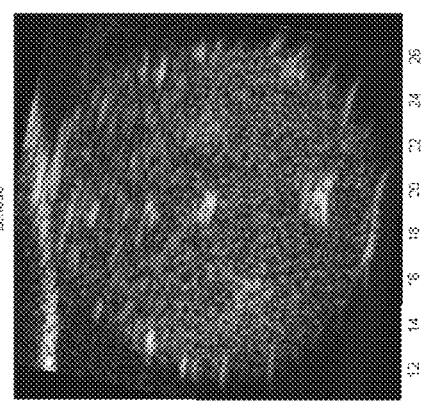
Figure 12A:
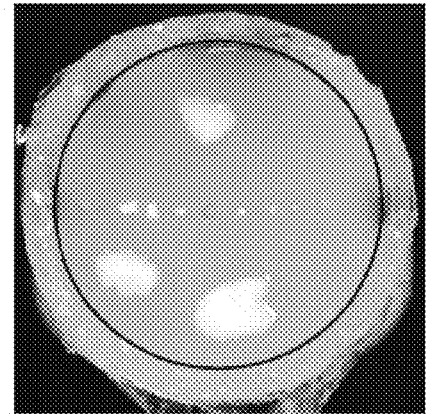

FIGS. 12A, 12B and 12C are images of a feedback signal using a Siemens® Antares Ultrasound machines, using VF 13-5 transduction at a nominal central frequency of 7.27 MHz, respectively: (A) phantom lesion; (B) B-mode image; and (C) complement image. These images are displayed with a non-linear (log) scale. Using the log scale, more details on the complement image are visible. The single-frame B-mode and complement images do not show considerable difference when the scales are adjusted. The rest of the images from FIG. 13B through FIG. 16C are illustrated on a log scale.

FIGS. 13A, 13B and 13C are images of the feedback signal of FIGS. 11A, 11B and 11C, but using angular compounding with five angular frames, to generate, respectively: (A) phantom lesion; (B) B-mode compound; and (C) complement compound. The fundamental difference between B-mode and complement images becomes more noticeable using an angular compounding technique. This technique may take frames at different angles around the phantom to achieve different scattering realizations. An average image denoted as compound image is generated by rotating and summing up these frames. The compound image has improved speckle contrast and further differentiates the B-mode and complement images. The images of FIGS. 13B and 13C are generated using five angular frames of the phantom. The differences between the B-mode and complement images start to appear.

FIGS. 14A, 14B and 14C are images of the feedback signal of FIGS. 11A, 11B and 11C, but using angular compounding with 13 angular frames, to generate, respectively: (A) phantom lesion; (B) B-mode compound; and (C) complement compound. As the number of angular frames increases, the complement image shows a greater number of details of the small inclusions. This improvement is achieved at the cost of more blurring in the boundaries as a result of the imperfections in the process of rotating the transducer around the phantom. Notice the suppressed inhomogeneity areas in the complement image and the distinctions of the smaller inclusions in the lower half of the lesion.

Figure 15C:
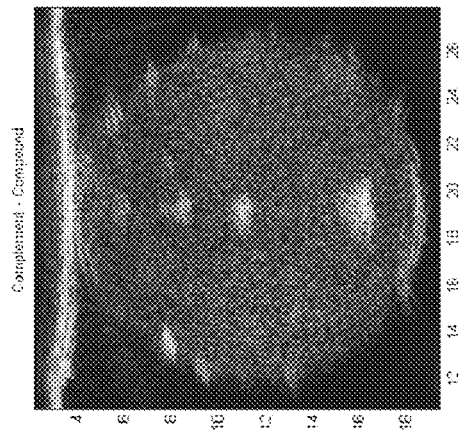
FIGS. 15A, 15B and 15C are images of the feedback signal of FIGS. 14A, 14B and 14C after switching to a higher nominal frequency of 11.42 MHz displayed in log scale, respectively: (A) phantom lesion; (B) B-mode compound; and (C) complement compound.
Figure 15B:
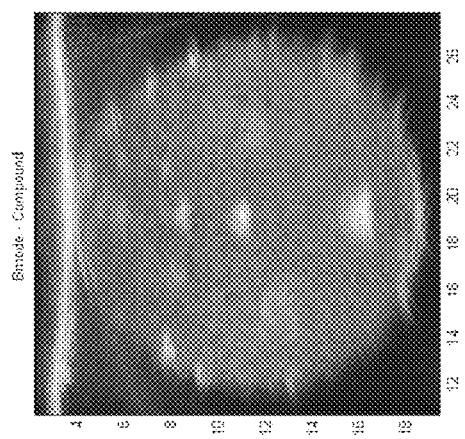
Figure 15A:
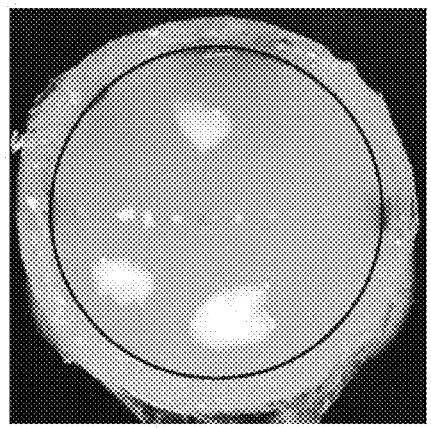

FIGS. 15A, 15B and 15C are images of the feedback signal of FIGS. 14A, 14B and 14C after switching to a higher nominal frequency of 11.42 MHz displayed in log scale, respectively: (A) phantom lesion; (B) compound B-mode image; and (C) compound complement image. As the frequency and bandwidth of the transducer increases, the baseband and side lobes of the acquisition information spectrum span a wider and higher frequency range and both the B-mode and complement images are expected to show more details of the small micrometer inclusions in the phantom. The images of FIGS. 15B and 15C are generated by combining 13 angular frames around the phantom with the transducer switched to a high nominal frequency of 11.42 MHz.

Figure 16C:
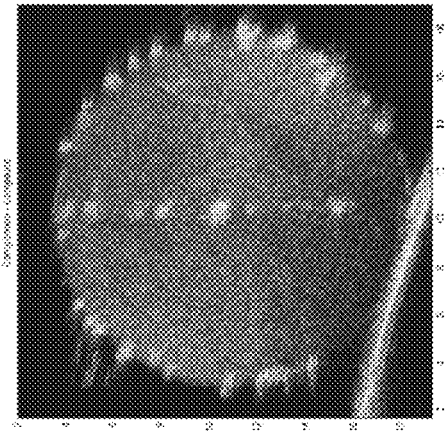
FIGS. 16A, 16B and 16C are images of the feedback signal of FIGS. 11A, 11B and 11C, but instead using a VEVO 2100 high-frequency ultrasound imaging system, in which the MS-250 transducer was operated at a nominal frequency of 16 MHz, respectively: (A) phantom lesion; (B) B-mode compound; and (C) complement compound.
Figure 16B:
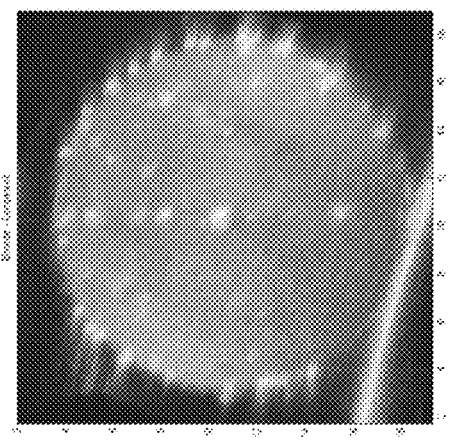
Figure 16A:
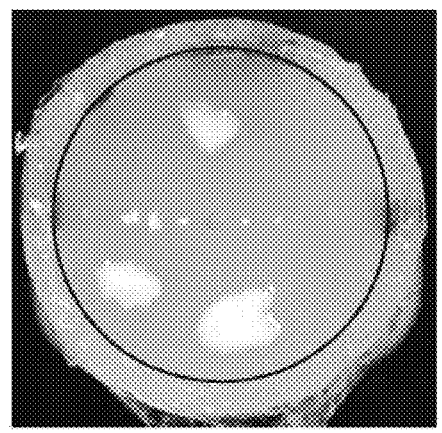

FIGS. 16A, 16B and 16C are images of the feedback signal of FIGS. 11A, 11B and 11C, but instead using a VEVO 2100 high-frequency ultrasound imaging system, in which the MS-250 transducer was operated at a nominal frequency of 16 MHz, respectively: (A) phantom lesion; (B) compound B-mode image; and (C) compound complement image. Once again, 13 angular frames around the phantom image were combined to generate a compound image. All nine inclusions are visible in the complement image while the inhomogeneities are filtered out.

Figure 17:
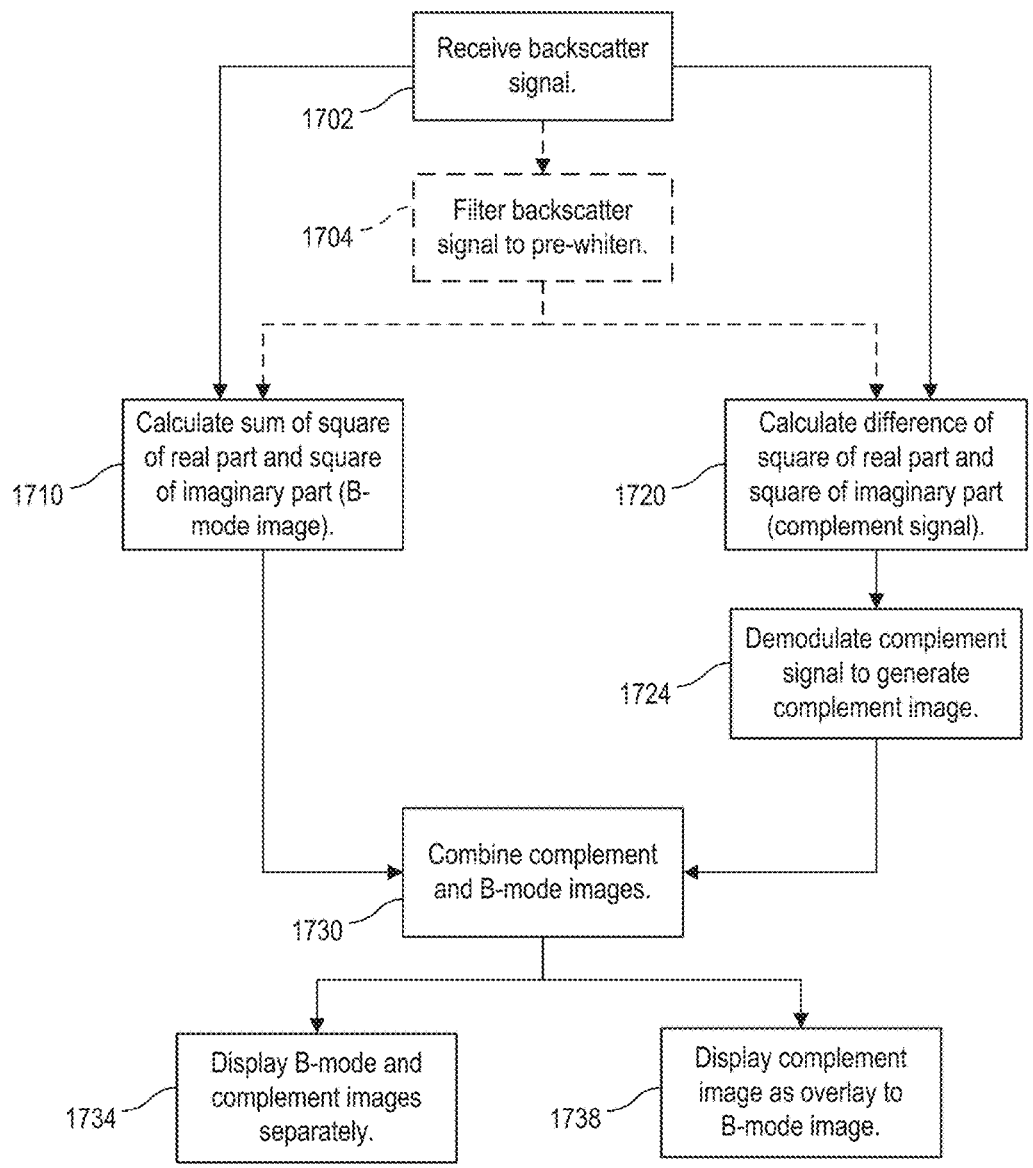
FIG. 17 is a flow chart of an exemplary method for generating both a B-mode and a complement image, which retrieves high spatial frequency information in sonography, according to an embodiment of the present disclosure.

FIG. 17 is a flow chart of an exemplary method for generating both a B-mode and a complement image, which respectively retrieves low and high spatial frequency information in sonography, according to an embodiment of the present disclosure. When using an imaging device such as an ultrasound machine, a transducer receives a backscatter (or echo) signal from a patient that includes RF data (1702). In one embodiment, a processing device of the imaging machine may filter the backscatter signal (such as with a Wiener filter) to prewhiten the RF data signal (1704). The processing device may then calculate a sum of a square of a real part and a square of an imaginary part of the RF data intensity, to generate an envelope signal that includes a mode-specific image (1710). In one example disclosed herein, the mode-specific image is a B-mode image.

The processing device may also calculate the difference of the square of the real part and the square of the imaginary part of the RF data intensity, to generate a complement signal (1720). The imaginary part is the 90-degree-phase-shifted version of the real part, or alternatively, a Hilbert transform of the RF data. The processing device may then demodulate the complement signal, to remove the carrier frequency and create a lower-frequency complement image suitable for displayed viewing (1724). The processing device may then combine the complement and B-mode images (1730).

In one example, the processing device may then display the B-mode and complement images separately in one or more display devices (1734) as diagnostic imaging. In another example, the processing device may display the complement image as an overlay on top of the B-mode image (1738) in a display device as diagnostic imaging. In one embodiment, the processing device may first threshold the complement image to detect and select microcalcifications, and color the microcalcifications before being combined with the B-mode image. This step may provide better visualization of the microcalcifications as distinguished from inhomogeneities in the combined image.

Figure 18:
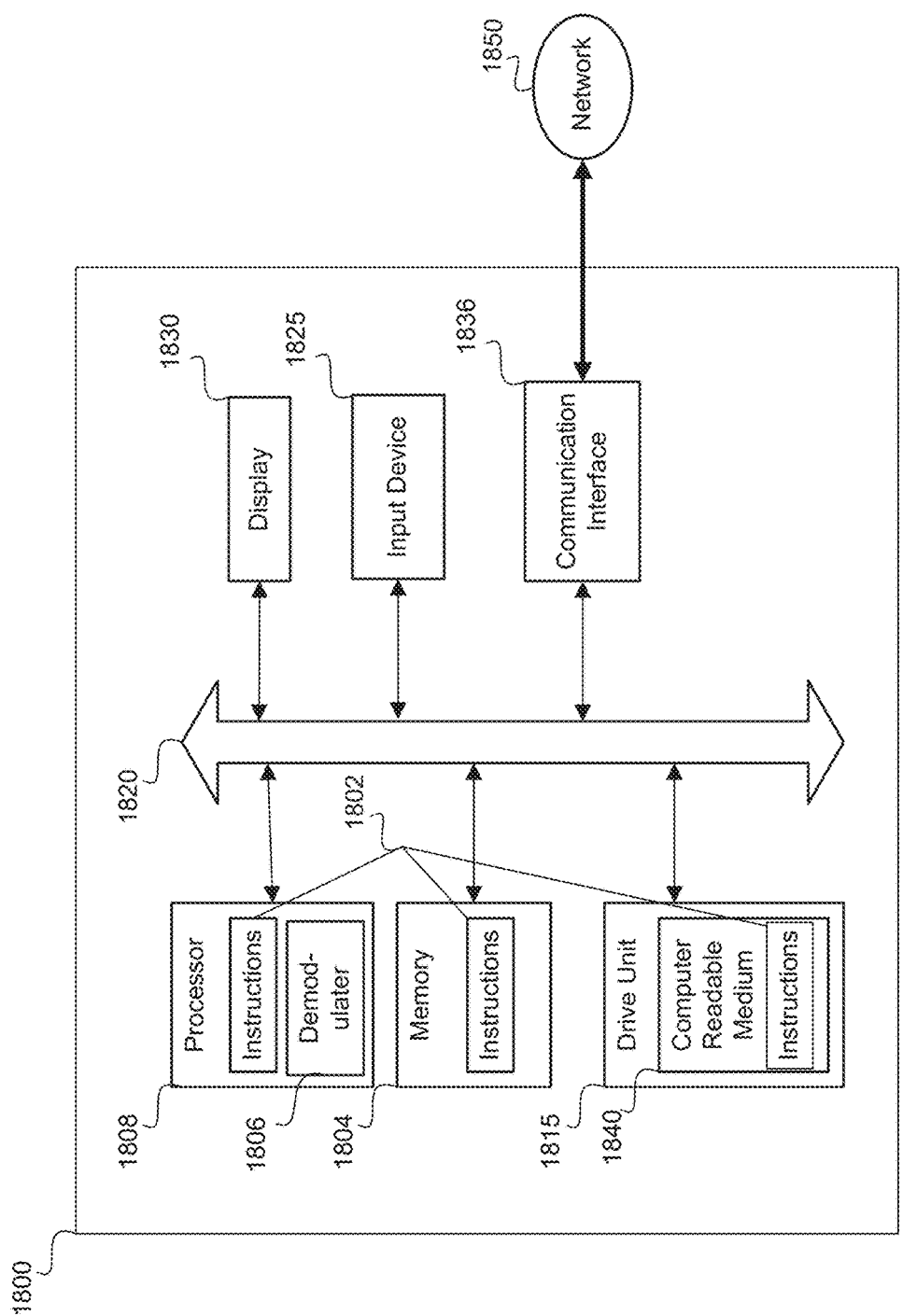
FIG. 18 is a computing system that may be used for retrieving high spatial frequency information in sonography according the embodiments disclosed herein.

FIG. 18 illustrates a computer system 1800, which may represent aspects of the imaging device 100 of FIG. 1, the processing device 110 or any other device or system to which is referred or which is capable of executing the embodiment as disclosed herein. The computer system 1800 may include an ordered listing of a set of instructions 1802 that may be executed to cause the computer system 1800 to perform any one or more of the methods or computer-based functions disclosed herein. The computer system 1800 may operate as a stand-alone device or may be connected to other computer systems or peripheral devices, e.g., by using a network 1810.

In a networked deployment, the computer system 1800 may operate in the capacity of a server or as a client-user computer in a server-client user network environment, or as a peer computer system in a peer-to-peer (or distributed) network environment. The computer system 1800 may also be implemented as or incorporated into various devices, such as a personal computer or a mobile computing device capable of executing a set of instructions 1802 that specify actions to be taken by that machine, including and not limited to, accessing the internet or web through any form of browser. Further, each of the systems described may include any collection of sub-systems that individually or jointly execute a set, or multiple sets, of instructions to perform one or more computer functions.

The computer system 1800 may include a memory 1804 on a bus 1820 for communicating information. Code operable to cause the computer system to perform any of the acts or operations described herein may be stored in the memory 1804. The memory 1804 may be a random-access memory, read-only memory, programmable memory, hard disk drive or any other type of volatile or non-volatile memory or storage device.

The computer system 1800 may include a processor 1808, such as a central processing unit (CPU) and/or a graphics processing unit (GPU). The processor 1808 may include one or more general processors, digital signal processors, application specific integrated circuits, field programmable gate arrays, digital circuits, optical circuits, analog circuits, combinations thereof, or other now known or later-developed devices for analyzing and processing data. The processor 1808 may implement the set of instructions 1802 or other software program, such as manually-programmed or computer-generated code for implementing logical functions. The logical function or any system element described may, among other functions, process and/or convert an analog data source such as an analog electrical, audio, or video signal, or a combination thereof, to a digital data source for audio-visual purposes or other digital processing purposes such as for compatibility for computer processing.

The processor 1808 may include a demodulator 1806 or contain instructions for execution by a demodulator 1806 provided a part from the processor 1808. The demodulator 1806 may include hardware and/or logic for executing the instructions to perform the demodulation and image generation as discussed in the present disclosure.

The computer system 1800 may also include a disk (or optical) drive unit 1815. The disk drive unit 1815 may include a non-transitory computer-readable medium 1840 in which one or more sets of instructions 1802, e.g., software, can be embedded. Further, the instructions 1802 may perform one or more of the operations as described herein. The instructions 1802 may reside completely, or at least partially, within the memory 1804 and/or within the processor 1808 during execution by the computer system 1800.

The memory 1804 and the processor 1808 also may include non-transitory computer-readable media as discussed above. A "computer-readable medium," "computer-readable storage medium," "machine readable medium," "propagated-signal medium," and/or "signal-bearing medium" may include any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium.

Additionally, the computer system 1800 may include an input device 1825, such as a keyboard or mouse, configured for a user to interact with any of the components of the computer system 1800. It may further include a display 1830, such as a liquid crystal display (LCD), a cathode ray tube (CRT), or any other display suitable for conveying information. The display 1830 may act as an interface for the user to see the functioning of the processor 1808, or specifically as an interface with the software stored in the memory 1804 or the drive unit 1815.

The computer system 1800 may include a communication interface 1836 that enables communications via the communications network 1810. The network 1810 may include wired networks, wireless networks, or combinations thereof. The communication interface 1836 network may enable communications via any number of communication standards, such as IEEE 802.11, IEEE 802.17, IEEE 802.20, each of the Institute for Electrical and Electronics Engineers WiMAX® of the WiMAX® Forum, WiFi® of the WiFi® Alliance, cellular telephone standards, or other communication standards.

Accordingly, the method and system may be realized in hardware, software, or a combination of hardware and software. The method and system may be realized in a centralized fashion in at least one computer system or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein. Such a programmed computer may be considered a special-purpose computer.

The method and system may also be embedded in a computer program product, which includes all the features enabling the implementation of the operations described herein and which, when loaded in a computer system, is able to carry out these operations. Computer program in the present context means any expression, in any language, code or notation, of a set of instructions intended to cause a system having an information processing capability to perform a particular function, either directly or after either or both of the following: a) conversion to another language, code or notation; b) reproduction in a different material form.

The above-disclosed subject matter is to be considered illustrative, and not restrictive, and the appended claims are intended to cover all such modifications, enhancements, and other embodiments, which fall within the true spirit and scope of the present disclosure. Thus, to the maximum extent allowed by law, the scope of the present embodiments are to be determined by the broadest permissible interpretation of the following claims and their equivalents, and shall not be restricted or limited by the foregoing detailed description. While various embodiments have been described, it will be apparent to those of ordinary skill in the art that many more embodiments and implementations are possible within the scope of the above detailed description. Accordingly, the embodiments are not to be restricted except in light of the attached claims and their equivalents, now presented or presented in a subsequent application claiming priority to this application.

What is claimed is:

1. An imaging system comprising:
   a display device;
   a transducer to transmit acoustic pulses modulated with a carrier frequency and to collect at least a portion of a high-frequency backscatter signal comprising radio frequency (RF) data;
   a processing device operatively coupled to the transducer and to the display device, the processing device to:
   calculate a summation of a square of a real part and a square of an imaginary part of the high-frequency backscatter signal, to generate an envelope signal comprising a first image suitable for display on the display device;

calculate a difference of the square of the real part and the square of the imaginary part of the high-frequency backscatter signal, to generate a complement signal that comprises high-frequency RF data lost during generation of the envelope signal;

demodulate the complement signal to generate a low-frequency complement image suitable for display on the display device with the envelope signal;

add the low-frequency complement imagine as an overlay to the first image to generate a combined image; and display the combined image on the display device as diagnostic imaging.

2. The imaging system of claim 1, wherein the high-frequency RF data comprises microcalcifications, and wherein the processing device is further to threshold the low-frequency complement image to filter out and select the microcalcifications.

3. The imaging system of claim 2, wherein the processing device is further to color the microcalcifications before adding the low-frequency complement image as an overlay to the first image.

4. The imaging system of claim 1, wherein the processing device is further to filter the high-frequency backscatter signal with a Wiener filter prior to generation of the envelope signal and the complement signal.

5. The imaging system of claim 1, wherein the real part comprises RF data intensity (g2) of the RF data and the imaginary part comprises a 90-degree shifted version of the RF data intensity (g2).

6. The imaging system of claim 1, wherein to collect at least a portion of the high-frequency backscatter signal, the transducer is further to employ an angular compounding technique to achieve different scattering realizations in the RF data.

7. A method comprising:

transmitting, by a transducer of an imaging device, acoustic pulses modulated with a carrier frequency;

collecting, by the transducer, at least a portion of a high-frequency backscatter signal comprising radio frequency (RF) data;

calculating, by a processing device of an imagining system, a summation of a square of a real part and a square of an imaginary part of the high-frequency backscatter signal, to generate an envelope signal comprising a first image suitable for display on a display device;

calculating, by the processing device, a difference of the square of the real part and the square of the imaginary part of the high-frequency backscatter signal, to generate a complement signal that comprises high-frequency RF data lost during generation of the envelope signal;

demodulating, by the processing device, the complement signal to generate a low-frequency complement image suitable for display on the display device with the envelope signal;

adding the low-frequency complement imagine as an overlay to the first image to generate a combined image; and displaying, by the processing device, the combined image on the display device as diagnostic imaging.

8. The method claim 7, wherein the high-frequency RF data comprises microcalcifications, the method further comprising thresholding the low frequency complement image to filter out and select the microcalcifications.

9. The method of claim 8, further comprising coloring the microcalcifications before adding the low-frequency complement image as an overlay to the first image.

10. The method of claim 7, further comprising filtering the high-frequency backscatter signal with a Wiener filter prior to generating the envelope signal and the complement signal.

11. The method of claim 7, wherein the real part comprises RF data intensity (g2) of the RF data and the imaginary part comprises a 90-degree shifted version of the RF data intensity (g2).

12. The method of claim 7, wherein the collecting at least a portion of the high-frequency backscatter signal further comprises employing an angular compounding technique to achieve different scattering realizations in the RF data.

13. A non-transitory computer-readable medium storing instructions that when executed by a processing device of an imaging system, cause the processing device to:

transmit, by a transducer of the imaging system, acoustic pulses modulated with a carrier frequency;

collect, by the transducer, at least a portion of a high-frequency backscatter signal comprising radio frequency (RF) data;

calculate a summation of a square of a real part and a square of an imaginary part of the high-frequency backscatter signal, to generate an envelope signal comprising a first image suitable for display on a display device;

calculate a difference of the square of the real part and the square of the imaginary part of the high-frequency backscatter signal, to generate a complement signal that comprises high-frequency RF data lost during generation of the envelope signal;

demodulate the complement signal to generate a low-frequency complement image suitable for display on the display device with the envelope signal;

add the low-frequency complement imagine as an overlay to the first image to generate a combined image; and display the combined image on the display device as diagnostic imaging.

14. The non-transitory computer-readable medium of claim 13, wherein the high-frequency RF data comprises microcalcifications, and wherein the instructions are further to cause the processing device to threshold the low-frequency complement image to filter out and select the microcalcifications.

15. The non-transitory computer-readable medium of claim 14, wherein the instructions are further to cause the processing device to color the microcalcifications before adding the low-frequency complement image as an overlay to the first image.

16. The non-transitory computer-readable medium of claim 13, wherein the instructions are further to cause the processing device to filter the high-frequency backscatter signal with a Wiener filter prior to generation of the envelope signal and the complement signal.

17. The non-transitory computer-readable medium of claim 13, wherein the real part comprises RF data intensity (g2) of the RF data and the imaginary part comprises a 90-degree shifted version of the RF data intensity (g2).

* * * * *